US008652789B2

(12) United States Patent
O'Mullan et al.

(10) Patent No.: US 8,652,789 B2
(45) Date of Patent: Feb. 18, 2014

(54) DIAGNOSIS AND PROGNOSIS OF DIPEPTIDYL PEPTIDASE-ASSOCIATED DISEASE STATES

(75) Inventors: Patrick O'Mullan, Jackson, NJ (US); Craig A. Gelfand, Jackson, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1358 days.

(21) Appl. No.: 11/724,029

(22) Filed: Mar. 13, 2007

(65) Prior Publication Data

US 2007/0264671 A1 Nov. 15, 2007

Related U.S. Application Data

(60) Provisional application No. 60/781,924, filed on Mar. 13, 2006, provisional application No. 60/804,397, filed on Jun. 9, 2006, provisional application No. 60/892,767, filed on Mar. 2, 2007.

(51) Int. Cl.
*G01N 31/00* (2006.01)
*G01N 33/53* (2006.01)

(52) U.S. Cl.
USPC ........ 435/7.21; 435/7.1; 435/287.9; 436/501; 436/518; 530/300; 530/350; 424/130.1; 424/9.1

(58) Field of Classification Search
None
See application file for complete search history.

(56) References Cited

U.S. PATENT DOCUMENTS

| | | | |
|---|---|---|---|
| 4,900,662 A | 2/1990 | Shah et al. |
| 5,202,234 A | 4/1993 | Shah et al. |
| 5,382,515 A | 1/1995 | Shah et al. |
| 5,382,522 A | 1/1995 | Shah et al. |
| 7,169,926 B1 | 1/2007 | Burgess et al. |

FOREIGN PATENT DOCUMENTS

WO   WO-2004/104216   12/2004

OTHER PUBLICATIONS

Mannucci, E. et al.; "Hyperglycaemia Increases Dipeptidyl Peptidase IV Activity in Diabetes Mellitus", Diabetologia, vol. 48, No. 6, Jun. 2005, pp. 1168-1172.
Lescuyer, P. et al.; "Prostaglandin D2 Synthase and Its Post-Translational Modifications in Neurological Disorders", Electrophoresis vol. 26, 2005, pp. 4563-4570.
Naohito, I. et al.; "Diagnostic Significance of Urinary Enzymes for Diabetes Mellitus and Hypertension", BIOSIS, 1995, XP-002300856.
Mavropoulos, J. et al.; "Anti-Tumor Necrosis Factor-α Therapy Augments Dipeptidyl Peptidase IV Activity and Decreases Autoantibodies to GRP78/BIP and Phosphoglucose Isomerase in Patients with Rheumatoid Arthritis", J. Rheumatology, vol. 32, No. 11, 2005, pp. 2116-2124.
Hartel-Schenk, S. et al.; "Distribution of Glycosyltransferases Among Golgi Apparatus Subfractions From Liver and Hepatomas of the Rat", Biochimica et Biophysica Acta, vol. 1115, No. 2, 1991, pp. 108-122.
O'Mullan, P. et al.; "Separation and Characterization of Dipeptidyl Peptidase IV Isoforms by Free Flow Electrophoresis", Diabetes, vol. 55, No. Suppl. 1, Jun. 2006, p. A438.
Ishii et al., "Diagnostic Significance of Urinary Enzymes for Diabetes mellitus and hypertension", Enzyme & Protein (1994) 95:vol. 48 No. 3, p. 174-182.
Kobayashi, Naoyuki,"Recent Progress of Free-Flow Electrophoresis Technique, and its Application to Proteomics", Protein Nucleic acid enzyme (2004) vol. 49, No. 9, p. 1333-1340.
Busek et al., Int. J. Biochem. Cell Biol. 36:408-421 (2004).
Sedo et al., Arthritis Res. Ther. 7:253-269 (2005).
Gorrell, Clinical Sci. 108:277-292 (2005).
Hartel et al., Histochemistry 89(2):151-161 (1988).
Yaron and Naider, Critical Rev. Biochem. Mol. Biol. 28(1):31-81 (1993).
Mattem et al., Scand. J. Immunol. 33:737 (1991).
Pethiyagoda et al., Clin. Exp. Metastasis 18(5):391-400 (2000).
Lambeir et al., J. Biol. Chem. 276(32):29839-29845 (2001).
Hildebrandt et al., Clin. Sci. (Lond.) 99(2):93-104 (2000).
Schon et al., Scand. J. Immunol. 29:127 (1989).
von Bonin et al., Immunol. Rev. 161:43-53 (1998).
Franco et al., Immunol. Rev. 161: 27-42 (1998).
Loster et al., Biochem. Biophys. Res. Commun. 217(1):341-348 (1995).
Johnson et al., J. Cell. Biol. 121:1423 (1993).
Vanhoof et al., Eur. J. Clin. Chem. Clin. Biochem. 30:333 (1992).
Raynaud et al., J. Cell. Physiol. 151:378 (1992).
Green et al., Diab. Vasc. Dis. Res. 3(3):159-165 (2006).
Wakselman et al., J. Dermatol. Sci. 22:152-160 (2000).
DiCarlantonio et al., Gamete Res. 15(2):161 175 (2005).
Mazzocco et al., FEBS Journal 273(5):1056 1064 (2006).
International Search Report, PCT/US07/06653.
Hurwitz, Medical News: Physicians Update, XXI(3); 1-5 (2006).
O'Connell et al., American Family Physician, 71(1); 105-11 (2005).
Smith et al., Aids Research and Human Retroviruses, 14(10); 851-868 (1998).
Entrez Gene Gene ID: 1075, Oct. 21, 2010.

*Primary Examiner* — Lisa Cook
(74) *Attorney, Agent, or Firm* — Lerner, David, Littenberg, Krumholz & Mentlik, LLP

(57) ABSTRACT

A method is provided for the diagnosis or prognosis of a disease state, involving the measurement of a parameter of discriminated dipeptidyl dipeptidases from a patient sample, and the correlation of the parameter with a disease.

47 Claims, 25 Drawing Sheets

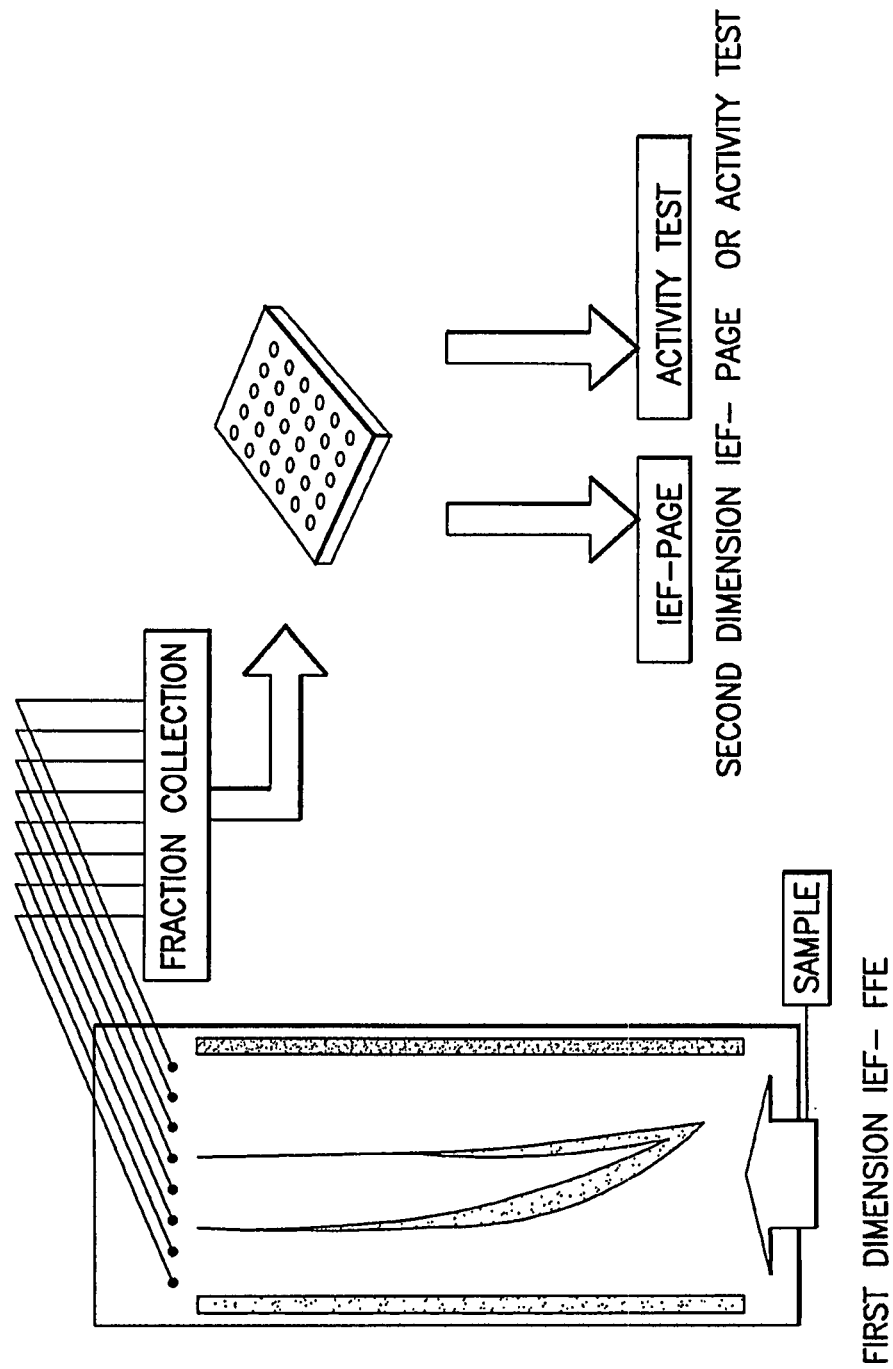

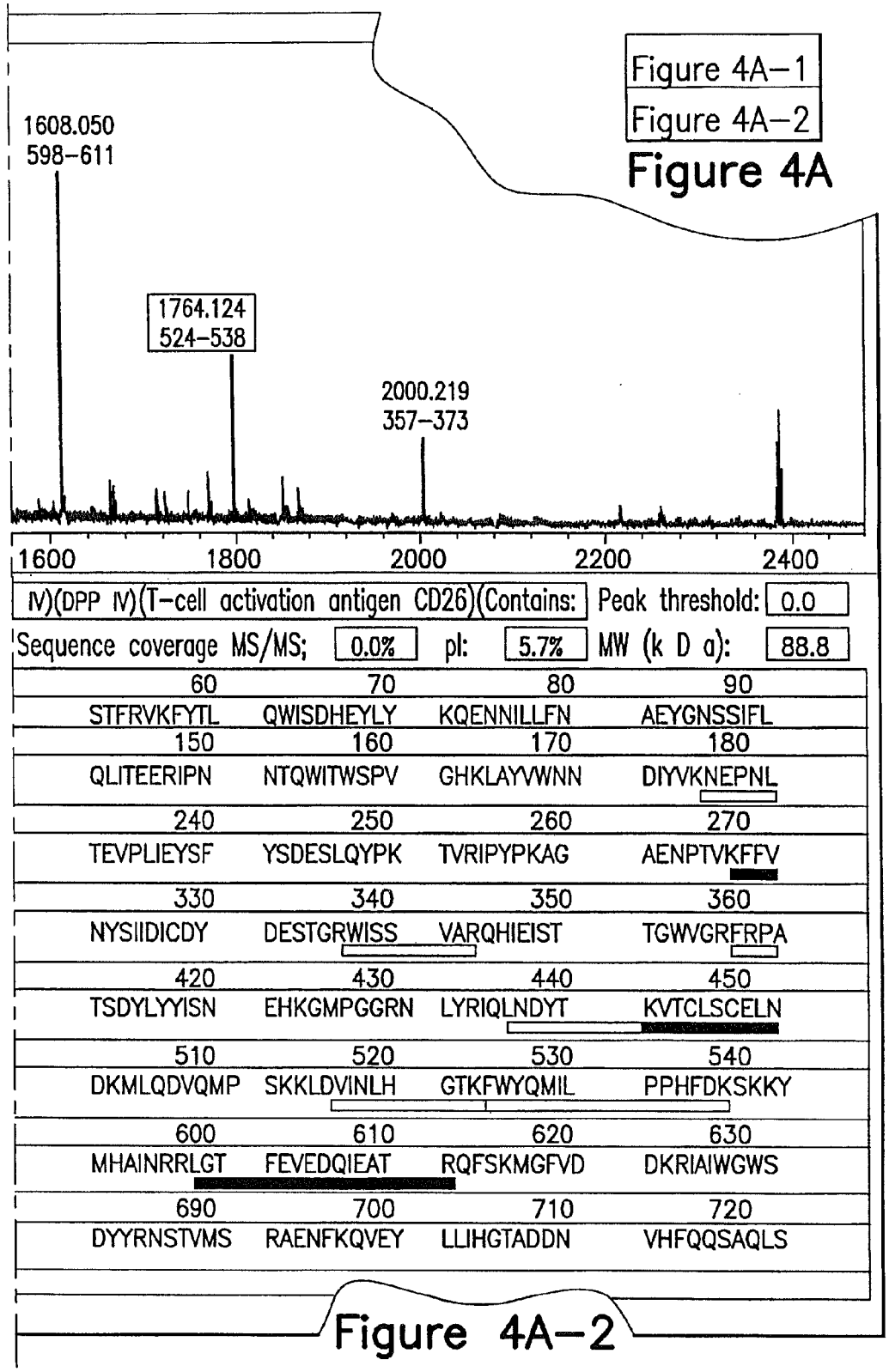

| | 10 | 20 | 30 | 40 | 50 | 60 | 70 | 80 | 90 | 100 |
|---|---|---|---|---|---|---|---|---|---|---|
| | MKTPWKVLLG | LLGIAAALVTV | TVPWLLNK | GTDDAAADSR | RTYTLIDYLK | STFRVKFYTL | QWISDHEYLY | KQENNILLFN | AEYGNSSIFL | ENSTFDELGY |
| | 110 | 120 | 130 | 140 | 150 | 160 | 170 | 180 | 190 | 200 |
| | STNDYSVSPD | RQFILFEYNY | VKQWRHSYTA | SYDIYDLNKR | QLITEERIPN | NTQWITWSPV | GHKLAYWNN | DIYKNEPNL | SSQRITWTGK | ENVYNGVTD |
| | 210 | 220 | 230 | 240 | 250 | 260 | 270 | 280 | 290 | 300 |
| | WYYEEVFSA | YSALWWSPNG | TFLAYAQFND | TEVPLIEYSF | YSDESLQYPK | TVRIPYPKAG | AENPTVKFFV | VDIRTLSPNA | SVTSYQIVPP | ASVLIGDHYL |
| | 310 | 320 | 330 | 340 | 350 | 360 | 370 | 380 | 390 | 400 |
| | CGWVTEER | ISLQWIRRAQ | NYSIIDICDY | DESTGRWISS | VARQHIEIST | TGWVGRFRPA | EPHFTSDGNS | FYKIISNEEG | YKHICHFQTD | KSNCTFITKG |
| | 410 | 420 | 430 | 440 | 450 | 460 | 470 | 480 | 490 | 500 |
| | AWEVIGIEAL | TSDYLYISN | EHKGNPGGRN | LYRIQLNDYT | KVTCLSCELN | PERCQYYSAS | FSNKAKYYQL | RCFGPGLPLY | TLHSSSSDKE | LRMLEDNSAL |
| | 510 | 520 | 530 | 540 | 550 | 560 | 570 | 580 | 590 | 600 |
| | DKMLQDVQMP | SKKLDVNLH | GTKFWYQMIL | PPHFDKSKKY | PLLIEVYAGP | CSQKVDTVFR | LSWATYLAST | ENIVASFDG | RGSGYQGDKI | MHAINRRLGT |
| | 610 | 620 | 630 | 640 | 650 | 660 | 670 | 680 | 690 | 700 |
| | FEVEDQIEAT | RQFSKHGFVD | DKRIAIWGWSYGGYVTSMVL | GAGSGVFKCG | IAVAPVSKWE | YDSVYTERY | MGLPTPEDNL | DYYRNSTVMS | RAENFKQVEY | |
| | 710 | 720 | 730 | 740 | 750 | 760 | 770 | | | |
| | LLIHGTADDN | VHFQQSAQLS | KALVDAGVDF | QTMWYTDEDH | GIASNMAHQH | IYTHHSHFLK | QCFSLP | | | |

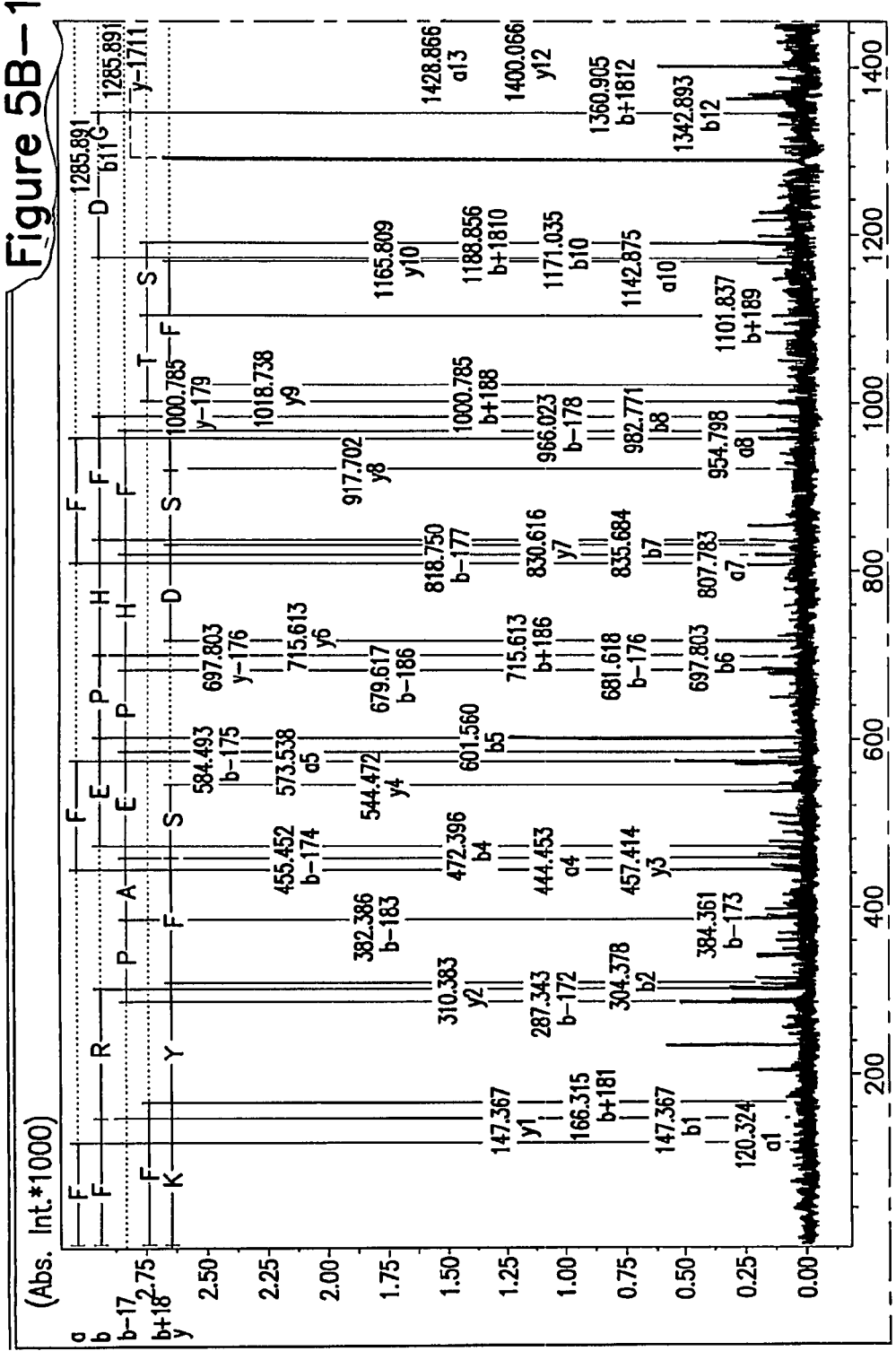

Figure 5B-4

| Peaks: | 200 | | Above Threshold: | 200 | | | |
|---|---|---|---|---|---|---|---|
| Assigned: | 57 | | Not Assigned: | 143 | | | |

| Pro | His | Phe | Thr | Ser | Asp | Gly | Asn | Ser |
|---|---|---|---|---|---|---|---|---|
| 6 | 7 | 8 | 9 | 10 | 11 | 12 | 13 | 14 |
| 670.367 | 807.426 | 954.494 | 1055.542 | 1142.574 | 1257.601 | 1314.623 | 1428.665 | 1515.698 |
| 698.362 | 835.421 | 982.489 | 1083.537 | 1170.569 | 1285.596 | 1342.617 | 1456.660 | 1543.692 |
| 681.335 | 818.394 | 965.463 | 1066.510 | 1153.543 | 1268.569 | 1325.591 | 1439.634 | 1526.666 |
| 680.351 | 817.410 | 964.479 | 1065.526 | 1152.559 | 1267.585 | 1324.607 | 1438.650 | 1525.682 |
| 716.373 | 853.432 | 1000.500 | 1101.548 | 1188.580 | 1303.607 | 1360.628 | 1474.671 | 1581.703 |
| 715.341 | 830.368 | 917.400 | 1018.448 | 1165.516 | 1302.575 | 1399.628 | 1528.670 | 1599.707 |
| 698.338 | 813.365 | 900.397 | 1001.445 | 1148.513 | 1285.572 | 1382.625 | 1511.668 | 1582.705 |
| 70.065 | 110.071 | 120.080 | 74.059 | 60.044 | 88.039 | 30.033 | 87.055 | 60.044 |
| Gly | Asp | Ser | Thr | Phe | His | Pro | Glu | Ala |

Figure 5B

| Figure.5B-1 | Figure.5B-2 |
|---|---|
| Figure.5B-3 | Figure.5B-4 | ical

DIAGNOSIS AND PROGNOSIS OF DIPEPTIDYL PEPTIDASE-ASSOCIATED DISEASE STATES

CROSS REFERENCE TO RELATED APPLICATIONS

This application claims the benefit of the filing date of U.S. Provisional Application No. 60/781,924 filed Mar. 13, 2006 and entitled "Method of Diagnosing Disease by Isoform Profiling", U.S. Provisional Application No. 60/804,397 filed Jun. 9, 2006 and entitled "Separation and Characterization of Dipeptidyl Peptidase IV Isoforms Using Free Flow Electrophoresis (FFE)", and U.S. Provisional Application No. 60/892,767 filed Mar. 2, 2007 entitled "Separation and Characterization of Dipeptidyl Peptidase IV Isoforms and/or Isozymes Using Matrix (Free Flow) Electrophoresis," the entire disclosures of which are hereby incorporated by reference herein.

SEQUENCE LISTING

The instant application contains a Sequence Listing which has been submitted in ASCII format via EFS-Web and is hereby incorporated by reference in its entirety. Said ASCII copy, created on May 10, 2011, is named Sequence Listing for Diagnosis and Prognosis of DPP Associated Disease States_ST25.txt and is 7.60 kilobytes in size.

FIELD OF THE INVENTION

The invention relates generally to the diagnosis and prognosis of diseases or conditions.

BACKGROUND OF THE INVENTION

Current methods for assessing risk for or diagnosing diseases often rely on a diagnosis by attrition, a process of elimination or by invasive surgery or biopsies. Even after a definitive diagnosis is obtained, the prognosis is generally based on subjective factors.

In certain diseases, such as metabolic disease, the methods by which an objective diagnosis may be made are often cumbersome, time-consuming and costly. For example, the primary method for diagnosing type 2 diabetes is the fasting plasma glucose test, which assesses blood sugar levels in plasma. This test requires the patient to fast for 8-14 hours, and often requires multiple blood draws over a period of hours to days. In addition, although the fasting plasma glucose test is useful in diagnosing the presence of type 2 diabetes, the test is very limited in its ability to provide a disease prognosis.

In medicine, there is a constant search for less invasive, less physically taxing, and more accurate ways to diagnose and treat diseases or conditions. As a greater understanding of biological processes, and the biochemistry associated with these processes, unfolds, certain theories have evolved about which compositions might be identified as markers or indicators for certain diseases or conditions. Proteases and peptidases, as a class, have been investigated for their utility in diagnosis and as targets for treating patients.

By way of general background, proteases/petpidases are typically classified by a number of criteria, such as site of action, substrate preference, and mechanism. For example, aminopeptidases act preferentially at the N-terminal residues of a polypeptide, carboxypeptidases act preferentially at the C-terminus, and endopeptidases act at sites between these two termini.

Dipeptidyl peptidases (DPPs) are peptidases that specifically cleave a dipeptide unit, i.e., a two amino acid unit, from their specific substrates. There are a number of different DPPs, and substrate preference is frequently expressed in terms of the amino acid residue immediately N-terminal to the cleavage site. For example, DPP-I (IUBMB Enzyme Nomenclature EC.3.4.14.1) is a lysosomal cysteine-type peptidase that releases an N-terminal dipeptide, Xaa-Yaa-|-Zaa- except when Xaa is Arg or Lys, or Yaa or Zaa is Pro. DPP-II (IUBMB Enzyme Nomenclature EC.3.4.14.2) is a lysosomal serine-type peptidase that releases an N-terminal dipeptide, Xaa-Yaa-|-, preferentially when Yaa is Ala or Pro. DPP-III (IUBMB Enzyme Nomenclature EC.3.4.14.4) is a cytosolic peptidase that has a broad activity on peptides, although it is highly selective for Arg-Arg-Z, where Z is any amino acid, at pH 9.2. DPP-IV (IUBMB Enzyme Nomenclature EC.3.4.14.4) is a membrane-bound serine-type peptidase that releases an N-terminal dipeptide from Xaa-Yaa-|-Zaa-, preferentially when Yaa is Pro, provided Zaa is neither Pro nor hydroxyproline.

DPPs are involved in a wide range of physiologically important activities, and have been associated with regulation of the neurological system, endocrine system, immune system and digestive system. DPP activity has been demonstrated in numerous intracellular and extracellular functions such as protein degradation and enzyme activation.

With regard to the specific DPPs mentioned previously, DPP-IV has been widely studied, along with its attendant isoforms and isozymes or structural homologs, and those proteins that exhibit DPP-IV-like activity. Proteins which exhibit DPP-IV-like activity have been termed dipeptidyl peptidase IV activity and/or structure homologs, or "DASH". DPP-IV is a type II membrane protein that is referred to by a number of names, including, but not limited to, DPP4, DP4, DAP-IV, FAP β adenosine deaminase complexing protein 2, adenosine deaminase binding protein (ADAbp), dipeptidyl aminopeptidase IV; Xaa-Pro-dipeptidyl-aminopeptidase; Gly-Pro naphthylamidase; postproline dipeptidyl aminopeptidase IV; lymphocyte antigen CD26; glycoprotein GP110; dipeptidyl peptidase IV; glycylproline aminopeptidase; glycylproline aminopeptidase; X-prolyl dipeptidyl aminopeptidase; pep X; leukocyte antigen CD26; glycylprolyl dipeptidylaminopeptidase; dipeptidyl-peptide hydrolase; glycylprolyl aminopeptidase; dipeptidyl-aminopeptidase IV; DPP IV/CD26; amino acyl-prolyl dipeptidyl aminopeptidase; T cell triggering molecule Tp103; X-PDAP. (Burgess et al., U.S. Pat. No. 7,169,926).

A number of DASH proteins have been reported, such as seprase, fibroblast activation protein a, DPP6, DPP8, DPP9, attractin, N-acetylated-α-linked-acidic dipeptidases I, II, and L, quiescent cell proline dipeptidase, thymus-specific serine protease and DPP IV-β (Busek et al., *Int. J. Biochem. Cell Biol.* 36:408-421 (2004)).

DPP-IV is constitutively expressed on epithelial and endothelial cells of a variety of different tissues, including intestine, liver, lung, kidney and placenta (Hartel et al., *Histochemistry* 89(2):151-161 (1988); Yaron and Naider, *Critical Rev. Biochem. Mol. Biol.* 28(1):31-81 (1993)). DPP-IV is expressed on circulating T-lymphocytes and has been shown to be synonymous with the cell-surface antigen, CD-26 (Sedo et al., *Arthritis Res. Ther.* 7:253-269 (2005)). In addition to a membrane-bound form, DPP-IV also exists in a soluble form, and DPP-IV activity can be found in body fluids such as blood plasma and synovial fluid (Sedo et al., *Arthritis Res. Ther.* 7:253-269 (2005); Gorrell, *Clinical Sci.* 108:277-292 (2005)).

DPP-IV is believed to play an important role in neuropeptide metabolism, T-cell activation, cell adhesion, digestion of proline containing peptides in the kidney and intestines, HIV infection and apoptosis, and regulation of tumorigenicity in certain melanoma cells (Mattem et al., *Scand. J. Immunol.* 33:737 (1991); Pethiyagoda et al., *Clin. Exp. Metastasis* 18(5):391-400 (2000)).

The natural substrates of DPP-IV include several chemokines, cytokines, neuropeptides, circulating hormones and bioactive peptides (Lambeir et al., *J. Biol. Chem.* 276(32):29839-29845 (2001)). A key regulatory role for DPP-IV, in the metabolism of peptide hormones and in amino acid transport, has been suggested. (Hildebrandt et al., *Clin. Sci. (Lond.)* 99(2):93-104 (2000)).

DPP-IV expression is increased in T-cells upon mitogenic or antigenic stimulation, suggesting a role in the immune system (Mattem et al., *Scand. J. Immunol.* 33:737 (1991)). Various other functions of T-lymphocytes such as cytokine production, IL-2 mediated cell proliferation and B-cell helper activity have also been shown to be dependent on DPP-IV activity (Schon et al., *Scand. J. Immunol.* 29:127 (1989)). In addition, DPP-IV appears to have a co-stimulatory function during T-cell activation and proliferation (von Bonin et al., *Immunol. Rev.* 161:43-53 (1998)).

DPP-IV is involved in other biological processes, including a membrane-anchoring function for the localization of the extracellular enzyme adenosine deaminase (ADA) (Franco et al., *Immunol. Rev.* 161: 27-42 (1998)) and participation in cell matrix adhesion by binding to collagen and fibronectin (Loster et al., *Biochem. Biophys. Res. Commun.* 217(1):341-348 (1995)).

DPP-IV is also believed to play a role in endocrine regulation and metabolic physiology. For example, DPP-IV cleaves the amino-terminal His-Ala dipeptide of glucagon like peptide-1 (GLP-1), generating a GLP-1 receptor antagonist, and thereby shortens the physiological response to GLP-1. DPP-IV has been implicated in the control of glucose metabolism because its substrates include the insulinotropic hormones GLP-1 and gastric inhibitory peptide (GIP), which are inactivated by removal of their two N-terminal amino acids. (Mannucci et al., *Diabetologia* 48:1168-1172 (2005)).

In addition to normal physiological function, DPPs have been studied for their role in disease states, including cancer, autoimmune disease, cardiovascular disease, metabolic disease and infectious disease.

For example, it has been suggested that DPP-IV is an adhesion molecule for lung-metastatic breast and prostate carcinoma cells (Johnson et al., *J. Cell. Biol.* 121:1423 (1993)). High DPP-IV activity has been found in tissue homogenates from patients with benign prostate hypertrophy and in prostatosomes (Vanhoof et al., *Eur. J. Clin. Chem. Clin. Biochem.* 30:333 (1992)).

High levels of DPP-IV expression have been found in human skin fibroblast cells from patients with the autoimmune diseases psoriasis, rheumatoid arthritis (RA) and lichen planus (Raynaud et al., *J. Cell. Physiol.* 151:378 (1992)).

DPP-IV has been associated with a number of metabolic diseases such as obesity and appetite regulation. For example, one of the more extensively studied DPP-IV-associated metabolic diseases is type 2 diabetes. Mannucci et al., defines and describes the relationships between chronic hyperglycemia and DDP-IV in diabetes. This research concludes that circulating DPP-IV activity directly correlates with the degree of hyperglycemia in type II diabetes.

Other studies discuss the relationship between DPP-IV and various hormones involved in the hormone cascade that regulates blood sugar levels. These studies conclude that DPP-IV degrades a hormone that is important for insulin secretion. Specifically, it has been suggested that DPP-IV degrades glucagon-like 1 peptide (GLP-1) which results in a decrease in insulin secretion and thus an increase in blood sugar. Based on this phenomenon, inhibitors of DPP-IV are being developed for the treatment of type II diabetes (Green et al., *Diab. Vasc. Dis. Res.* 3(3):159-165 (2006)).

DPP-IV is apparently essential for the penetration and infectivity of HIV-1 and HIV-2 viruses in $CD4^+$ T-cells (Wakselman et al., *J. Dermatol. Sci.* 22:152-160 (2000)). Therefore, there is some suggestion that suppression of DPP-IV might suppress this mechanism as well.

Recently, some avenues of DPP research have focused on the manipulation of DPP levels as a means for developing treatments and therapies for the DPP-associated disease states and conditions. However, few treatments and therapies have resulted from this work to date.

SUMMARY OF THE INVENTION

The development of therapies and diagnostic tools that are based on DPP and its role in biological processes are still sought. An embodiment of the invention described herein is directed to a method for prognosis or diagnosis of a DPP-associated disease state or condition. Specifically, one or more parameters of discriminated portions of a specific DPP is measured and the measurement is correlated with the presence, absence or severity of the disease state or condition.

Another embodiment of the invention described herein is directed to a method for prognosis or diagnosis of a DPP-associated disease state or condition. Specifically, one or more parameters of discriminated portions of DPP isoforms is measured and the measurement is correlated with the presence, absence or severity of the disease state or condition.

A further embodiment of the described invention is directed to a method for the diagnosis or prognosis of type II diabetes. Specifically, at least one parameter of one or more discriminated portions of DPP-IV isoforms from a patient sample is measured and the measurement is correlated with the presence, absence or severity of type II diabetes.

DETAILED DESCRIPTION

Figure 2A:
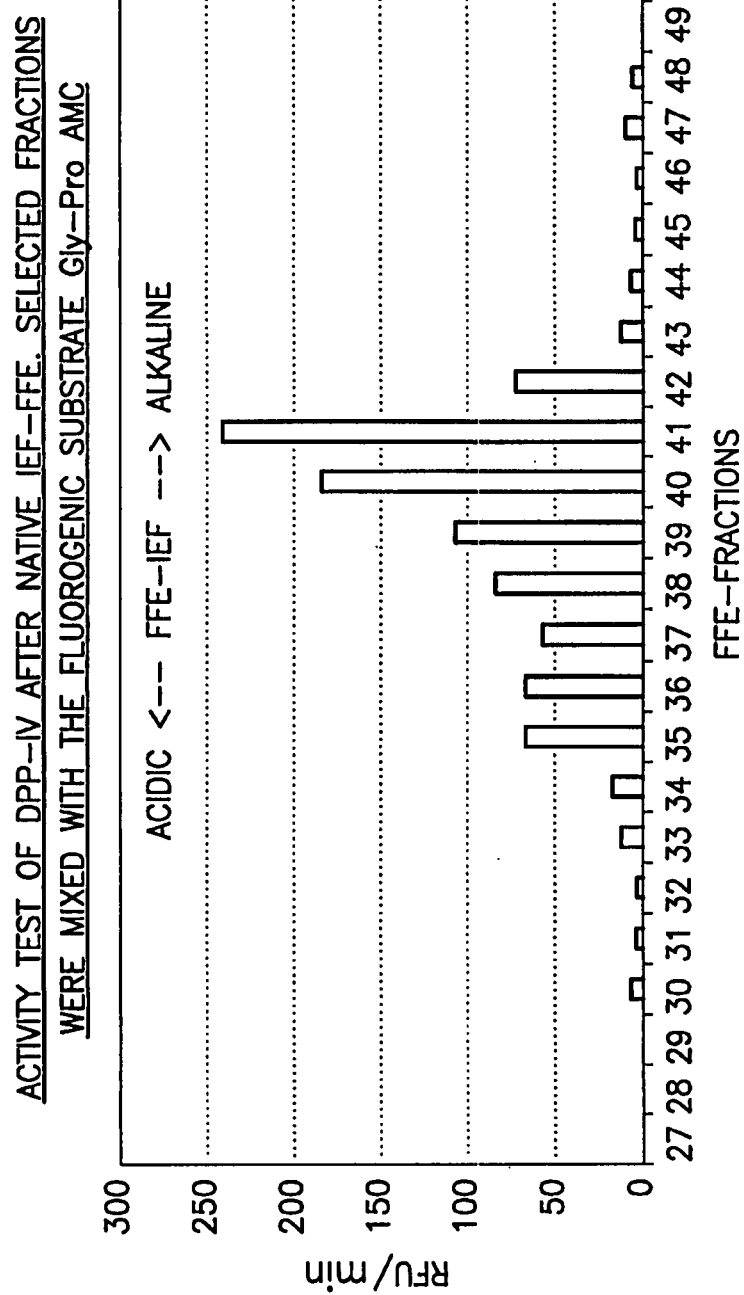
FIGS. 2A and B are graphs showing the results of an activity test of porcine DPP-IV after native IEF-FFE.

The methods described herein provide for the risk assessment, diagnosis or prognosis of a dipeptidyl peptidase (DPP)-associated disease state or condition. In particular, the described methods relate to a method of risk assessment, diagnosis or prognosis of a disease state or condition associated with a particular DPP parameter. According to embodiments of the described method, a parameter of a discriminated DPP portion is measured. The measurement is then correlated with the presence, absence or severity of said disease state or condition.

For the purposes of this application, the terms "protease" and "peptidase" are used interchangeably, and refer to enzymes that catalyze the hydrolysis of peptidic amide bonds. Dipeptidyl peptidases (DPPs) are proteases which cleave a dipeptide unit from a polypeptide.

As used herein, the term "discriminated portions of a specific DPP" refers to a specific DPP (e.g., one or more isoforms from a specific DPP family, e.g., DPP-I, DPP-II, DPP-III, DPP-IV, etc.) from a patient sample that have been distinguished, separated or isolated from each other in some manner.

In one embodiment, the specific DPP is subjected to some condition that will distinguish at least one isoform of the specific DPP from at least one other isoform of the DPP. Each discriminated portion may contain one or more DPP isoforms of the specific DPP, and some portions may contain no DPP isoforms. In another embodiment, DPP (which may include DPP of one family or more than one family) is subjected to some condition that will distinguish at least one isoform of the DPP from at least one other isoform of the DPP.

Specifically, the individual DPP isoforms may be completely or only partially discriminated into portions and from each other. Thus, one discriminated portion may contain one or more isoforms, or each discriminated portion may only contain one isoform. Likewise, one discriminated portion may contain one isoform, while other discriminated portions contain more than one isoform. Additionally, some discriminated portions may contain no DPP isoforms as long as one or more other portions contain one or more DPP isoforms.

The specific DPP may be a member of any specific DPP or DASH family, including DPP-I, DPP-II, DPP-III or DPP-IV. In exemplary embodiments, the DPP is DPP-IV. DPP that is not designated as specific includes both non-specific and specific DPP.

As used herein, the term "isoform" of a DPP refers to any of multiple forms of one or more DPP enzymes which differ in some physical way, but which all have a common characteristic catalytic activity, homologous primary structure/amino acid sequence or are derived from the same genetic loci. The catalytic activity of DPP isoforms need not be identical in degree or rate of catalysis, only in a common substrate profile. Likewise, the primary structure of the isoforms need not be identical, but may be the result of minor additions, deletions, or mutations in the amino acid sequence of the enzyme.

Isoforms may have similar or the same primary structure and may have the same catalytic activity or differing catalytic activity or activities. The primary structure of the isoforms may significantly differ while retaining the same catalytic activity. Isoforms may have the same or different secondary structure, tertiary structure, and/or quaternary structure, but still be isoforms of one another as long as they retain the same or similar primary structure and/or enzymatic activity and/or are derived from the same genetic loci.

Isoforms may be derived from the same genetic locus, or from different genetic loci. They may be the result of different alleles; multiple genetic loci; alternative splicing of messenger RNA produced from the same gene; or the result of post-translational modification, such as addition of polysaccharide, phosphate, sulfhydryl, sialic acid, or other groups.

"Isoforms", when used herein, also include isozymes. As used herein, the term "isozyme" (alternatively, isoenzyme) is a type of isoform which refers to any of the multiple forms of an enzyme arising from a genetically determined difference in primary structure/amino acid sequence.

Any group of enzymes which share the same catalytic activity, genetic loci or primary structure are isoforms of one another. Multiple DPP isoforms are known. For example, DPP-1 exists in at least 2 isoforms derived from transcript variants encoding from the same gene (Entrez Gene GeneID: 1075). Likewise, multiple isoforms have been reported for DPP-II (DiCarlantonio et Gamete Res. 15(2):161 175 (2005)), DPP-III (Mazzocco et al., FEBS Journal 273(5): 1056 1064 (2006)) and DPP-IV (Schmauser et al., Glycobiol. 9(12):1295 1305 (1999)).

For example, any enzyme which cleaves post-proline dipeptide bonds is a DPP-IV isoform. One skilled in the art is readily aware of the many isoforms of DPP. Not all isoforms are identified herein. By way of illustration, and not limitation, DPP-IV isoforms include, but are not limited to DPP-IV; the various sialated forms of DPP-IV; membrane-bound DPP-IV; soluble DPP-IV; and any of the dipeptidyl peptidase IV activity and/or structure homologs (DASH), such as seprase, fibroblast activation protein α, DPP6, DPP8, DPP9, attractin, N-acetylated-α-linked-acidic dipeptidases I, II, and L, quiescent cell proline dipeptidase, thymus-specific serine protease and DPP IV-β.

DPP parameters which may be measured include amount, concentration, activity, expression, or amount or type of post-translational modification.

"Amount" of DPP includes the presence, absence or quantity of DPP. "Activity" of DPP includes the presence, absence, quantity, degree, or rate of enzymatic activity, including the specific activity. "Expression" of DPP includes the presence, absence, rate or quantity of DPP expression. "Concentration" of DPP is the amount of DPP isoform per unit volume present in a portion.

The DPP parameter may be measured directly or indirectly and may be qualitative or quantitative.

DPP activity may be measured using any assay which can quantitatively or qualitatively measure DPP activity. Assays suitable for measuring the activity of DPP include assays which detect the presence or amount of a hydrolysis product of DPP activity on a detectably labeled substrate. The label may be directly or indirectly detectable, and may be fluorogenic, chemiluminescent, calorimetric, or radioactive. Fluorogenic labels include 7-amino-4-methylcoumarin (AMC) and 7-amino-4-trifluoromethylcoumarin (AFC).

As will be understood by those of skill in the art, the mode of detection of the signal will depend on the exact detection system utilized in the assay. The detection system may detect mass changes, changes in amino acid sequence or peptide length, chromogenic changes, or flurogenic changes. The detection method may employ secondary detection schemes including secondary enzymatic reactions that result in the detectable change, among a wide variety of detection schemes described in the art.

For example, if a radiolabeled detection reagent is utilized, the signal will be measured using a technology capable of quantitating the signal from the biological sample or of comparing the signal from the biological sample with the signal from a reference sample, such as scintillation counting, autoradiography (typically combined with scanning densitometry), and the like. If a chemiluminescent detection system is used, then the signal will typically be detected using a luminometer. If a fluorescent detecting system is used, fluorescence can be measured using a spectrofluourometer. Methods for detecting signal from detection systems are well known in the art.

In some embodiments, DPP activity is measured via an assay which detects presence or amount of a hydrolysis product of DPP activity on a detectably labeled substrate. DPP-IV activity may be measured using an assay that detects hydrolysis of any detectably labeled substrate which would be catalyzed by DPP-IV, i.e., X-Y-R, wherein X is any amino acid; Y is Pro (Proline), Ala (Alanine) or Arg (Arginine); and R is any directly or indirectly detectable label.

DPP amount may be measured using any assay which can quantitatively or qualitatively measure the amount of one or more DPP isoforms. Assays suitable for measuring the amount of DPP include, but are not limited to, western blot analysis, protein spectrophotometry, radioimmunoassay, competitive-binding assays, and ELISA assays. In this regard, antibodies which are specific for one or more DPP isoforms are particularly useful.

DPP concentration may be measured using any assay which can quantitatively or qualitatively measure the concentration of one or more DPP isoforms. Assays suitable for measuring the concentration of DPP include western blot analysis, protein spectrophotometry, radioimmunoassay, competitive-binding assays, and ELISA assays. In this regard, antibodies which are specific for one or more DPP isoforms are particularly useful.

DPP expression may be measured using any assay which can quantitatively or qualitatively measure the expression of one or more DPP isoforms. Assays suitable for measuring the expression of DPP generally detect DPP mRNA or protein, and include northern blot analysis and western blot analysis or variations thereof (e.g., Far Western Analysis, microarray chips).

Type or degree of post translational modification may be measured using any assay which can quantitatively or qualitatively measure the modification of one or more DPP isoforms. Assays suitable for measuring the type or degree of post translational modification include lectin binding, western blot analysis, protein spectrophotometry, radioimmunoassay, competitive-binding assays, and ELISA assays.

One or more than one parameters may be measured. For example, a single parameter (e.g., amount, concentration, activity, expression, amount or type of post translational modification) may be measured. Alternatively, two or more parameters may be measured, for example both amount and concentration, amount and activity, amount and expression, concentration and activity, concentration and expression, or activity and expression may be measured. Likewise, amount, activity and expression; amount, concentration and expression; or concentration, activity and expression may be measured.

If two or more measurements are taken, they may be taken concurrently or consecutively. For example, amount may be measured at the same time as activity. Alternatively, amount may be measured before or after activity. If three or more measurements are taken, they may also be taken consecutively or concurrently. For example, amount may be measured before post-translational modification type and activity, where post-translational modification type and activity are measured concurrently, or amount, post-translational modification type and activity are each measured concurrently or consecutively with respect to each other. Likewise, if more measurements are taken, they may be taken concurrently or consecutively with respect to each other, or grouped in each possible way, such that each group is taken concurrently or consecutively with respect to every other group. In other words, each of the measurements may be grouped in a factorial or distributive manner, and each group can be measured, with respect to all the other groups, either consecutively or concurrently.

In addition to multiple measurements, any given measurement, whether of one or more parameters, may be taken more than once, i.e., repeated, for any given patient sample.

Additionally, any combination of measurements may be taken with respect to the portions. For example, a single parameter may be measured for one, some or all of the portions. Likewise, more than one parameter may be measured for one, some or all of the portions. A single parameter may be measured for one or some portions, while another parameter is measured for other or all portions. For example, the amount may be measured for only one portion, while the activity of all portions may be measured. Likewise, the activity of only one portion may be measured, while the amount of all portions may be measured.

When measuring one or more DPP parameters, the patient sample may be divided into a number of aliquots, with separate aliquots used to measure different DPP parameters or perform replicate measurements. Additionally or alternatively, each of the discriminated DPP portions may be divided into a number of aliquots for measurement of different DPP parameters or replicate measurements. Replicate measurements are not necessary to the methods of the invention, but many embodiments of the invention will utilize replicate testing, particularly duplicate and triplicate testing.

Alternately, the patient sample or an aliquot therefrom may be tested to determine the levels of multiple DPP parameters in a single reaction using an assay capable of measuring the individual levels of different DPP parameters in a single assay, such as an array-type assay or assay utilizing multiplexed detection technology (e.g., an assay utilizing detection reagents labeled with different fluorescent dye markers).

As used herein, the term "DPP-associated disease or condition" refers to those diseases or conditions that are characterized by a difference in one or more particular measurable DPP parameters. DPP-associated diseases or conditions are not necessarily caused by a change in DPP, but can be diagnosed or monitored by measuring one or more DPP parameters.

DPP-associated disease states and conditions include, but are not limited to, metabolic disease, autoimmune disease, cancer and viral infections.

Metabolic disease(s), as the term is used herein, are disorders of metabolism and include both acquired and genetic diseases. A number of them are described in Harrison's Principles of Internal Medicine. In general, metabolic disease are divided into three main classes, glycogen storage disease (i.e., those diseases affecting carbohydrate metabolism, such as type II diabetes), fatty acid oxidation disorders (i.e., those disorders affecting the metabolism of fat components, such as Fabry's Disease), and mitochondrial disorders (i.e., those disorders affecting the mitochondria, such as Leigh Syndrome).

Metabolic disease states which can be detected with the present invention include, but are not limited to: Type-II Diabetes, Hypoglycemia, Hyperglycemia, Graves' Disease, Cushing's Syndrome, Alkaptonuria, Albinism, Histidinemia, Hyperornithinemia, Wilson's disease, Tay-Sachs' Disease, Niemann-Pick disease, Krabbe's disease, Paget's, maple syrup urine disease or phenylketonuria. In an exemplary embodiment, the DPP is DPP-IV, and the disease is type II diabetes.

Autoimmune diseases which can be detected with the present invention include, but are not limited to: rheumatoid arthritis, lichen planus, psoriasis, uveitis, hemolytic anemias, rheumatic fever, Crohn's disease, Guillain-Barre syndrome, psoriasis, thyroiditis, Graves' disease, myasthenia gravis, glomerulonephritis, autoimmune hepatitis, or systemic lupus erythematosus. In certain embodiments, the autoimmune disease is psoriasis, rheumatoid arthritis or lichen planus, and the DPP is DPP-IV.

Cancers which can be detected with the present invention include, but are not limited to: primary and metastatic solid tumors and carcinomas of the breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries, choriocarcinoma and gestational trophoblastic disease; male genital tract including prostate, seminal vesicles, testes and germ cell tumors; endocrine glands including thyroid, adrenal, and pituitary; skin including hemangiomas, melanomas, sarcomas arising from bone or soft tissues and Kaposi's sarcoma; tumors of the brain, nerves, eyes, and meninges including astrocytomas, gliomas, glioblastomas, retinoblastomas, neuromas, neuroblastomas, Schwannomas and meningiomas; solid tumors arising from hematopoietic malignancies such as leukemias and including chloromas, plasmacytomas, plaques and tumors of mycosis fungoides and cutaneous T-cell lymphoma/leukemia; lymphomas including both Hodgkin's and non-Hodgkin's.

Viral infections which can be detected with the present invention include, but are not limited to those infections caused by viral families which are pathogenic for humans and other animals such as: Adenoviridae, Birnaviridae Bunyaviridae, Coronaviridae Flaviviridae, Herpesviridae, Orthomyxoviridae Papovaviridae, Parvoviridae Picornaviridae Reoviridae Retroviridae (e.g., HIV), Rhabovirdae, or Togaviridae. In certain embodiments, the DPP is DPP-IV, and the viral disease is HIV.

As used herein, the term "patient" refers to any living organism, in need of a diagnosis, prognosis, disease progression monitoring, or risk assessment of a DPP-associated disease state or condition, and wherein the patient possesses the physiology associated with DPP expression. Such patients include, but are not limited to humans, higher primates, other mammals (e.g., domesticated mammals such as cats, dogs and horses, rodents such as rats and mice, and wild animals such as lions, tigers and bears), avians (e.g., chickens, parakeets) and other animals.

As used herein, the term "patient sample" or "biological sample" refers to any sample taken from or coming from a patient that might be expected to contain the target enzyme, and includes both cellular and acellular samples. Patient samples include, but are not limited to tissues, such as muscle, liver, lung, spleen, adipose, mammary and tumor tissue; blood and blood products, such as whole blood, plasma, serum and blood cells; and other biological fluids, such as urine, saliva, tears, mucus, amniotic fluid, cerebrospinal fluid, synovial joint fluid and seminal fluid. Patient samples may also contain a combination of fluids and/or tissues.

Samples may be procured from a patient by any clinically acceptable method such as venipuncture, spinal tap, amniocentesis and tissue biopsy.

Although samples may be used directly as obtained from the patient, one aspect of the invention contemplates the processing of samples prior to discriminating the DPP into portions (e.g., discriminating DPP isoforms into portions) or measuring the DPP parameter. Processing includes, but is not limited to, homogenizing, diluting, concentrating, sonicating, freezing, mixing with a preservative or other agent, or combinations thereof.

Additionally, samples which contain cells or other tissues wherein the DPP might be expected to be membrane-bound may be processed so as to release the DPP from the cell membrane, thus allowing it to be utilized in any of the art recognized methods for separating/isolating proteins/enzymes from a sample. Methods of releasing membrane-bound proteins are well-known in the art and include freeze/thawing, homogenization, sonication, and chemical or enzymatic release of the active enzyme from the membrane.

In some examples, the patient sample is collected in a container comprising EDTA, protease inhibitors, or some other component suitable for transport, preservation, and treating of a biological sample.

When the patient sample constitutes a fluid, processing may include the form of elimination of nucleated and/or non-nucleated cells, such as erythrocytes, leukocytes, and platelets in blood samples (for example, in order to obtain plasma), or may also include the elimination of certain proteins, such as certain clotting cascade proteins from blood (for example, in order to obtain serum). For example, blood may be collected in a container with heparin, citrate, or protease inhibitors or contacted with heparin, citrate or protease inhibitors upon collection.

Additional processing may include concentrating or diluting a sample so as to, for example, normalize the total protein content prior to discrimination or measurement. Protocols for performing these activities are well known in the art.

After the correlation between the measurement of the DPP parameter with the disease state or condition is made, the result may be communicated to an operator. The result includes the presence, absence or severity of a disease state or condition.

An "operator" can be a doctor, nurse, physician's assistant, medical technician, laboratory technician, or anyone operating a machine or apparatus which performs one or more steps of the invention, or anyone who may receive the diagnosis or prognosis information, including the patient. For example, the diagnosis or prognosis information may be automatically communicated to the patient or patient's representative via facsimile, telephone, text messaging, or email.

Any means for conveying the result may be used, and include, but are not limited to, displaying the disease state in a medium such as an electronic screen, a digital screen, or a printable substrate; effecting an audible signal, such as a buzzer, a bell, an electronically generated voice, or a recorded voice; via telephone, text messaging, email or facsimile.

The DPP isoforms may be partially or completely discriminated into DPP portions prior to or simultaneously with the measurement of any DPP parameters. For example, assuming there are more than two types of DPP isoforms present in a sample, the isoforms may be discriminated into only two portions, each one including more than one type of isoform (i.e., partially discriminated); or the isoforms may be discriminated into portions wherein each portion only contains one type of isoform (i.e., completely discriminated). Likewise the isoforms may be partially discriminated into two or more portions, one portion containing only one type of isoform, and other portions containing more than one type of isoform.

The DPP portions may be discriminated by any means, including physical separation or isolation or other methods of identifying or distinguishing isoforms from one another.

For example, discrimination can be based on difference in biochemical properties, such as electrophoretic mobility or isoelectric point (pI); heat stability; molecular weight; amino acid sequence, in the case of isoforms differing by primary structure; antibody affinity or avidity; extent or type of post-translational modifications; and kinetic properties, such as $K_m$ or rate constant.

Antibodies or lectins specific for different DPP isoforms may be used to either physically separate the DPP portions, or distinguish the portions without physical separation. For example, antibodies specific for each different DPP isoform may carry a different detectable label, requiring no physical separation to discriminate the portions. Alternatively, the antibodies may be used on a support or column to physically separate different DPP isoforms into portions.

Methods for separation include isoelectric focusing, which separates based on pI; electrophoretic methods, either in a matrix such as a gel or filter, or gel-free, which can distinguish based on electric charge and/or molecular weight; extent of lectin binding or variety of lectins having affinity to the isoforms; antibody binding; and affinity or size-discriminating chromatography methods.

As used herein, the term "isoelectric point" (pI) is the pH at which a molecule carries no net electrical charge. The pI is also referred to as an isoelectric pH. Thus, for the purposes of this application, the term "pI" and "isoelectric pH" are used interchangeably. In an exemplary embodiment, the DPP portions are discriminated based on pI, and the specific DPP is DPP-IV.

Methods of isoelectric focusing include free flow electrophoresis, isoelectric focusing electrophoresis, or chromatofocusing or other solid-phase mediated separation facilitated by flowing a buffer system changing in pH over time past the solid-phase.

In isoelectric-focusing electrophoresis, a sample of interest is injected or administered directly into a gel slab, filter, or other medium containing an immobilized pH gradient The pH gradient runs parallel to the direction of the electric field, and the protein(s) in the sample are separated from each other by migrating, in one direction, through the different pH environments before reaching a pH environment that is equivalent to its pI.

Once a protein has reached its pI, it will be immobile within the matrix material. At this point, a sample can be obtained from the matrix material and utilized in further analyses such as, sodium dodecyl sulfate polyacrylamide gel electrophoresis (SDS-PAGE) (Zuo et al., *Analytical Biochem.* 284:266-278 (2000)), a second dimension separation on a planar chip, (Becker et al., *J. Micromech. Microeng.* 8:24 28 (1998)), an assay for detecting enzyme activity such as fluorometry, or an assay suitable for measuring any of the DPP parameters.

Free-flow electrophoresis is an electrophoresis method that uses no solid matrix such as the acrylamide gels in traditional electrophoresis, or the separation phases used in chromatography. Instead, analytes are separated according to their charge and/or electrophoretic mobility in a continuous laminar flow or buffer solution in an electric field applied perpendicular to the flow direction.

An example of a machine which performs free flow electrophoresis is the BD™ Free Flow Electrophoresis System (Becton Dickenson model #441117). Utilizing this system, discriminated samples are collected in 96 capillaries at the end of a separation chamber, which allows for the continuous fractionation to flow into a collection divide in which the outflow remains physically separated into a plurality of fractions. This method is suitable for separating samples via at least three separation principles: Isoelectric focusing (IEF), Zone electrophoresis (ZE), and Isotachophoresis (ITP). Once collected, the fractions can be further analyzed via any of the assays described for use after isoelectric focusing, i.e., SDS-PAGE, second dimension separation on a planar chip and enzyme activity assays.

The discrimination and measurement are not limited to any particular order. Discrimination may take place prior to or after parameter measurement, or concurrently with measurement. For example, the specific DPP may be physically separated into portions using a method such as electrophoresis, and then one or more parameters of some or all of the portions may be measured.

Alternatively, when measurement and discrimination are done concurrently, the specific DPP may be discriminated into portions by, for example, contacting the patient sample with antibodies specific for different DPP isoforms, each of the antibodies linked to a different detectable label, while the signals from the detectable labels are measured.

In another embodiment, the portions or isoforms can be discriminated using a dual detection system. For example, the DPP isoforms can be contacted with a solid phase-bound antibody which binds to all or most DPP isoforms and one or more antibodies or lectins specific for a smaller portion of DPP isoforms. Each of the more specific antibodies or lectins contain a unique detectable label. The isoforms can be contacted with both antibodies or the antibody and lectins simultaneously, or in either series, e.g., contacted with the bound antibody and then the more specific antibody/lectin or with the more specific antibody/lectin and then the bound antibody.

The DPP may be discriminated into two or more portions. The number of portions depends on the degree of discrimination desired, and the method of discrimination performed. There is no limitation on the number of portions into which the DPP may be discriminated, but, for example, the DPP may be discriminated into 2 or more portions, such as 2, 3, 4, 5, 6, 7, 8, 9, 10, 11, 12, 18, 24, 36, 48, 96, 100, 200, 300, 384, 400, 500 or 1536 portions. For example, in some embodiments, it is convenient to discriminate DPP isoforms into, for example, 96 portions to allow for handling and parameter measurement in standard 96 well plates.

For complete discrimination of isoforms, each DPP portion should contain no more than one DPP isoform, and some portions may contain no DPP isoforms. For partial discrimination of isoforms, at least one DPP portion should contain more than one DPP isoform, while other portions may contain no DPP isoforms, one DPP isoform, or more than one DPP isoform.

In certain embodiments of the invention, patient samples are obtained from an individual at more than one time point. Such "serial" sampling is well suited for determination of the early onset of a disease, prior to the onset of typical medical abnormalities, and thus facilitating earlier remedial therapeutic strategies that could lead to more effective disease management or even disease avoidance. Such serial sampling is also well suited for the aspects of the invention related to monitoring progression of a disease, for example, type II diabetes, in a patient. This is especially useful for assessing effectiveness of any treatment that the patient may be undergoing in connection with the disease. Serial sampling or repeated sampling may also be useful for determining individual risk for developing the disease or condition.

Serial sampling can be performed on any desired timeline, such as hourly, semi-daily, daily, weekly, monthly, quarterly (i.e., every three months), semi-annually, annually, biennially, or less frequently. The comparison between the measured levels and the reference level may be carried out each time a new sample is measured, or the data relating to levels may be held for less frequent analysis.

The measuring or discrimination preferably takes place ex vivo or in vitro. In one embodiment, both the measurement and discrimination takes place ex vivo.

As will be appreciated by one of skill in the art, methods disclosed herein may include the measurement of any of a variety of DPP or non-DPP parameters (which may or may not be disease related parameters) to determine the integrity and/or characteristics of the patient sample. For example, estrogen levels, which are generally higher in females, may be measured as a marker of gender, or other chemical blood measurements such as cholesterol levels.

Other disease-related non-DPP parameters may be measured, to confirm the diagnosis or prognosis. In some embodiments, the non-DPP parameter is hemoglobin A1C level, and the disease is diabetes. Hemoglobin A1C levels below 7% of overall hemoglobin is indicative of the absence of diabetes; levels above 7% of overall hemoglobin is indicative of the presence of diabetes. The non-DPP parameter may be measured before or after the DPP parameter, or it may be measured simultaneously.

In order to correlate the measured DPP parameter to a disease state or condition, the measured DPP parameter may be compared to a reference, i.e., a standard or an internal control. An increase, decrease, or shift in DPP parameter, either individually or additively, as compared to a reference, either positive or negative, may correlate with a disease state.

Alternatively, the DPP parameter of a portion of the discriminated enzymes may be compared to parameter of another portion of discriminated enzymes, or it may be compared to the total measurement of two or more discriminated portions.

Of course, the measured parameter should be compared to a corresponding parameter. For example, if DPP amount is measured, then the value for DPP amount should be compared to the value for DPP amount of a reference or other portion. If DPP expression is measured, it should be compared to DPP expression of a reference or other portion.

In certain embodiments, the parameter of a continuous range of portions is measured. For example, for isoforms separated on the basis of isoelectric point, one or more parameters of two or more portions separating at adjacent pH or isoelectric points may be measured.

A profile of the measured parameter(s) may be obtained over the continuous range of portions. Alternatively, a profile of the measured parameter(s) may be obtained based on the measurements of a non-continuous range of portions. The profile may be based on all portions, or it may be based on a subset of portions.

Figure 14:
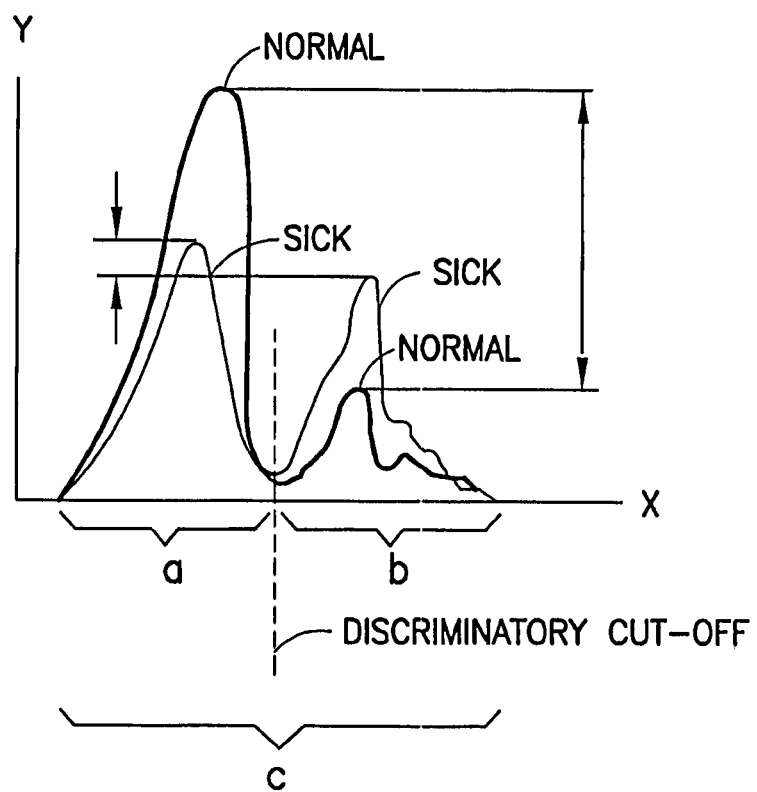
FIG. 14 is a graph depicting the various ways in which measured parameters of discriminated DPP isoforms can be correlated with disease.

The various comparisons that may be made between and among the various portions to determine correlation with disease state are numerous. Techniques for analyzing the data for which the measured parameter or for comparing the data with other data are well known to one skilled in the art. Consequently, all such techniques are not discussed in detail herein. One exemplary technique for analyzing the data in order to draw the desired conclusion (i.e., the presence or absence of a disease state) is illustrated by referring to the graph in FIG. 14. In FIG. 14, the y-axis depicts the level of a DPP parameter (e.g., activity, expression, amount, concentration, type or amount of post-translational modification). The x-axis depicts the dimension of discrimination (e.g., pI, pH, or isoform type).

Referring to the graph, three areas are highlighted, area "a," area "b" and area "c." For each area, the total measurement within a range (e.g., area under curve for a given range) may be measured giving values "a" and "b", totaling value "c". Other values which may be measured include peak value within a range, point at which the peak value is reached within a range, specific activity at any point in the range (for example, at a specific pI or pH), the points at which the measured parameter increases or decreases (e.g. an inflection point), shifts in measured parameter along the x-axis compared to other measurements, and any combinations thereof. The values may be calculated based on a profile obtained by measuring a continuous range of portions, or they may be calculated based on measurements of single or a plurality of portions.

In order to correlate a disease state with one of the measurements, one could compare a range "a" value(s) to the range "b" value(s); the range "a" value(s) to the range "c" value(s); the range "b" value(s) to the range "c" value(s); the range "a" value(s) to an internal control or standard; the range "b" value(s) to an internal control or standard; and/or the range "c" value(s) to an internal control or standard.

Alternatively, discrete quantitative measurements in any range or any ratio of such quantitative measurements associated with a given dimension or dimensions of discrimination can be made and compared to known reference values or ranges of values for such measurements, with the reference range having been established through clinical trials to provide a scale by which to determine the presence, absence or severity of the disease. Quantitative measurements may also be supplemented by inclusion of an internal or external standard, run either simultaneously or in series with the dimension of discrimination (e.g. isoform discriminations) that can be used to normalize the quantitative read-out to the pre-established reference ranges.

As used herein, the term "standard" refers to a value, generally an average, median or mean value, obtained from a segment of the population. The standard may be a positive standard or a negative standard, and may be obtained from an age-matched population. Age-matched populations (from which standard values may be obtained) are ideally the same age as the individual being tested, but approximately age-matched populations are also acceptable. Approximately age-matched populations may be within 1-20 years, including about 1, about 5, about 10, about 15 or about 20 years of the age of the individual tested, or may be groups of different ages which encompass the age of the individual being tested. Approximately age-matched populations may be in 2, 3, 4, 5, 6, 7, 8, 9, or 10 year increments (e.g., a "5 year increment" group which serves as the source for standard values for a 62 year old individual might include 58-62 year old individuals, 59-63 year old individuals, 60-64 year old individuals, 61-65 year old individuals, or 62-66 year old individuals).

A positive standard refers to a value, for example, an average value, which is obtained from a segment of the population with the particular disease state. A negative standard refers to a value, for example, an average value, which is obtained from a segment of the population without the particular disease state.

As used herein, the term "internal control" refers to a value obtained from a sample or samples from single patient or group of patients whose disease state is known. An internal control may be a positive control, a negative control, or a same-patient control. For example, the internal control may be a positive control from a patient or patients with the particular disease state; or it may be a negative control from a patient or patients with the particular disease state. Finally, an internal control may be a value obtained from the patient to be diagnosed, either from a sample derived from a different physical site (i.e., blood vs. liver), at a different time to measure disease progression, or from two or more samples which have been processed differently prior to measurement, or collected in separate containers which can be the same type or different types (e.g., two EDTA plasma tubes or one EDTA plasma and one serum tube).

The internal control value may be obtained concurrently or contemporaneously with the measurement for the patient to be diagnosed, or it may be obtained at some other time.

The results of the comparison between the measured value(s) or between the measured value(s) and reference value(s) are used to diagnose or aid in the diagnosis or prognosis of a disease, to stratify patients according to the severity of their disease, or to monitor progression of a disease in a particular patient. Accordingly, if the comparison indicates a difference (that is, an increase or decrease) between the measured value(s) and the reference value(s) that is suggestive/indicative of disease, then the appropriate diagnosis is aided in or made. Conversely, if the comparison of the measured level(s) to the reference level(s) does not indicate differences that suggest or indicate a disease diagnosis, then the appropriate diagnosis is not aided in or made.

When more than one disease related DPP parameter is measured, but the various measurements do not unanimously suggest or indicate a diagnosis of disease, the "majority" suggestion or indication (e.g., when the method utilizes four disease related DPP parameters, three of which suggest/indicate disease) is used. Such a result would be considered as suggesting or indicating a diagnosis of disease for the individual.

The process of comparing a measured value and a reference value can be carried out in any convenient manner appropriate to the type of measured value and reference value for the diabetic related DPP parameter at issue. "Measuring" can be performed using quantitative or qualitative measurement techniques, and the mode of comparing a measured value and a reference value can vary depending on the measurement technology employed. For example, when a qualitative assay is used to measure DPP activity levels, the levels may be compared by visually comparing the intensity of the fluorescing reaction product, or by comparing data from a spectrophotometer (e.g., comparing numerical data or graphical data, such as bar charts, derived from the measuring device). However, it is expected that the measured values used in the methods of the invention will most commonly be quantitative values (e.g., quantitative measurements of concentration, such as nanograms of DPP isoform per milliliter of sample, or absolute amount). In other examples, measured values are qualitative. As with quantitative measurements, the comparison can be made by inspecting the numerical data, and by inspecting representations of the data (e.g., inspecting graphical representations such as bar or line graphs).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for DPP parameter(s) Alternately, a separate device (e.g., a digital computer) may be used to compare the measured value(s) and the reference value(s). Automated devices for comparison may include stored reference values for the disease related DPP parameter(s) being measured, or they may compare the measured value(s) with reference values that are derived from contemporaneously measured reference samples.

In some embodiments, the methods of the invention utilize "simple" or "binary" comparison between the measured level(s) and the reference level(s), e.g., the comparison between a measured level and a reference level determines whether the measured level is higher or lower than the reference level. In some embodiments, any difference in value may indicate disease.

As described herein, parameters may be measured quantitatively (absolute values) or qualitatively (relative values). The respective disease related DPP parameter(s) levels for a given assessment may or may not overlap. As described herein, for some embodiments, qualitative data indicate a given level of disease state (mild, moderate or severe) and in other embodiments, quantitative data indicate a given level of disease state.

In certain aspects of the invention, the comparison is performed to determine the magnitude of the difference between the measured and reference values, e.g., comparing the "fold" or percentage difference between the measured value and the reference value. A fold difference that is about 2 times lower or higher than some minimum fold difference suggests or indicates for example, the presence of a disease. A fold difference can be determined by measuring the absolute amount, concentration, activity or expression of a DPP and comparing that to the absolute value of a reference, or a fold difference can be measured by the relative difference between a reference value and a sample value, where neither value is a measure of absolute amount, concentration, activity or expression, and/or where both values are measured simultaneously. Alternatively, fold differences may be measured within the test data themselves, for instance by comparing the fold difference of "a" to "c" as compared to "b" to "c", or any other such ratios of measurable parameters within the assay system. Accordingly, the magnitude of the difference between the measured value and the reference value that suggests or indicates a particular diagnosis will depend on the particular parameter being measured to produce the measured value and the reference value used.

As described herein, there is a correlation between the DPP-IV activity profile obtained from a continuous range of DPP-IV isoforms separated by pI and the presence, absence or severity of type II diabetes. This correlation is used in a method for the diagnosis or prognosis of type II diabetes comprising measuring one or more DPP-IV parameters of discriminated DPP-IV portions from a patient sample, and correlating said measured DPP-IV parameter with the presence, absence or severity of type II diabetes in the patient. In certain embodiments, the DPP-IV parameter is DPP-IV activity. In certain embodiments, the DPP-IV portions are discriminated based on pI.

The DPP-IV parameter may be compared to a population standard or an internal control. Any difference from a negative population standard or a negative internal control can be correlated with presence or severity of diabetes. The higher degree of difference between the measured DPP-IV parameter and the negative reference, the more severe the prognosis. Likewise, any difference from a positive population standard or a positive internal control can be correlated with the absence of diabetes. As discussed above, parameters include activity, amount, expression or concentration.

The DPP-IV portions may be discriminated by any characteristic or method disclosed herein. In exemplary embodiments, the DPP-IV portions are discriminated based on pI. In certain embodiments, the DPP-IV portions are separated by free flow electrophoresis.

Figure 10:
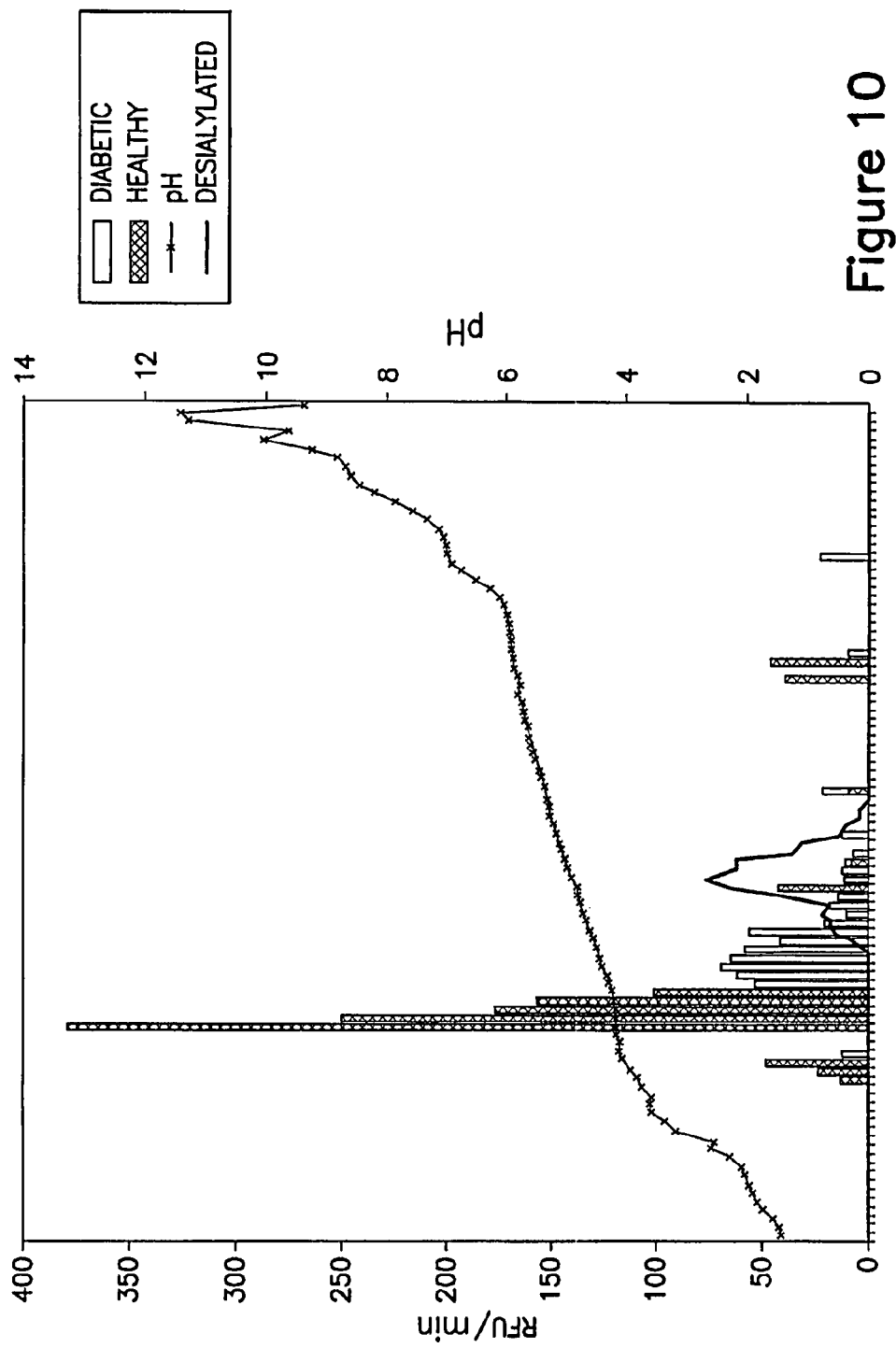
FIG. 10 shows the comparison of DPP-IV activity between pI discriminated DPP-IV isoforms in plasma from a healthy (light bars) and a diabetic (dark bars) patient, as well as disialylated isoforms from a diabetic patient (dark line). The dotted line represents the pH at which each portion was discriminated.

FIG. 10 shows the comparison of DPP-IV activity profile between pI discriminated DPP-IV portions in plasma from one healthy and one diabetic patient. The present inventors have shown that, in diabetic patients, the DPP-IV activity profile shifts to a higher pH. Any difference in DPP-IV activity profile at any point or points from the value from any healthy patient shown here, or any difference in DPP-IV activity profile at any point or points from the value obtained from an internal negative control or population standard, can be correlated with diabetes.

Thus, a shift in DPP-IV activity profile from any negative standard shown herein or a population negative standard to higher pH is indicative of diabetes. Likewise, a shift in DPP-IV activity profile from an internal negative control to higher pH is indicative of the presence of type II diabetes. The more pronounced the shift in activity profile, the more severe the disease.

A positive standard, associated with an extreme measurement "opposite" of a healthy sample or population, can be represented by measurement of the most extreme isoform within the pI range in question. Such a positive standard could be established, for example, by treatment of the patient sample with chemical or enzymatic methods to completely remove all glycosylations, in the event that the complete absence of all glycans represented the measurable isoform condition furthest from the isoforms contained in typical healthy samples. It should be noted that an extreme isoform resulting from this treatment may never actually be possible within actual samples, but can still be used to establish the furthest possible range of pH, for purposes of providing a measurable control for the assay. As an alternative, this "extreme" positive isoform could be an external control, which might be measured separately or measured after spiking into the sample being analyzed. In certain embodiments, such a positive control could also be used to assist in normalization of the resulting sample measurements.

By "shift" in activity is meant any difference in DPP-IV activity in one or more DPP-IV portions. For example, the measured value for DPP-IV activity may differ from the reference in only one discriminated portion, or it may differ in some or all portions. Trends in DPP-IV activity level, for example, higher activity level at higher pH, are especially useful for detecting type II diabetes.

Diabetic patients and healthy patients also display two main peaks in DPP-IV activity profile when DPP-IV is discriminated based on pI. Diabetic patients tend to display peaks at about pH 4.4 and about pH 4.8. Each of these peaks is associated with about 10% of the total measured activity of the pI discriminated isoforms. Healthy patients tend to display peaks at about pH 3.9 and about pH 4.1.

By "peak" is meant one of a small number of the local extreme values for all values measured. Each value is associated with a discriminated portion. A peak value may be associated with one discriminated portion or a group of discriminated portions. That value may therefore by a discrete value for a single discriminated portion or an integration of the discrete values for a range of discriminated portions. For example, a profile of values as function of discriminated portions may contain only one peak, or it may contain more than one peak. Generally, only the top 1, 2, 3, 4, or 5 values will be considered peaks. Optionally, for example, the peak may be a value related, preferably at or near the profile from a plurality of adjacent values, wherein the values change from a rise to a falling magnitude.

Thus, a maximum peak in DPP-IV activity of pI discriminated DDP-IV isoforms at or about pH 3.9 and/or at or about pH 4.1 can be correlated with the absence of diabetes.

Likewise, a peak in DPP-IV activity of pI discriminated DPP-IV isoforms at or about pH 4.4 and/or at or about pH 4.8 can be correlated with the presence of diabetes. Peaks which are at least about 10% of the total measured activity of the continuous range of DPP-IV are especially useful for the presence of diabetes. The higher the peak at or about pH 4.4 and/or pH 4.8, the more severe the diagnosis.

Figure 11:
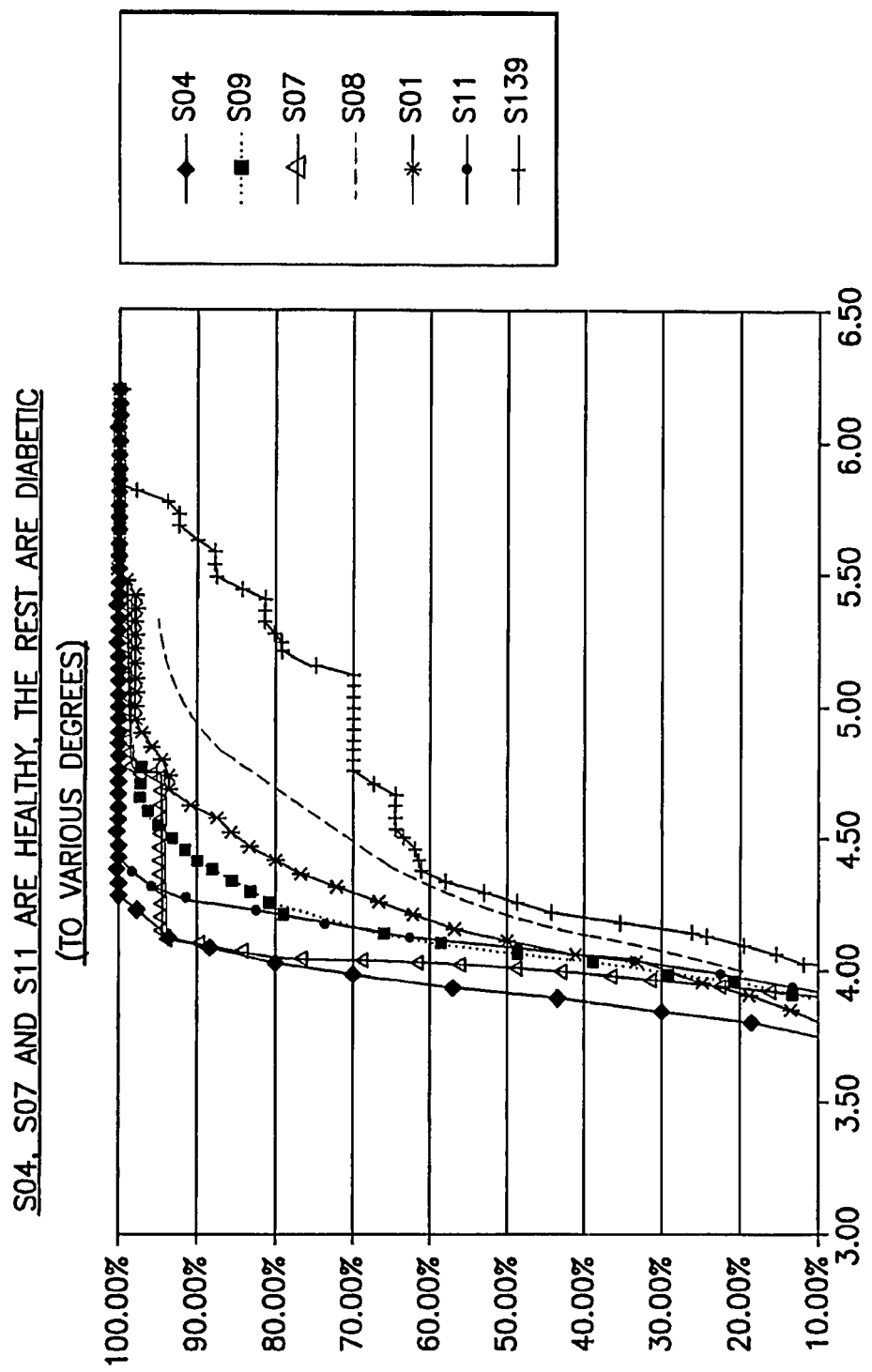
FIG. 11 is a breakout plot of the pH vs. DPP-IV activity of pI discriminated DPP-isoforms from healthy and diabetic patients. S04, S11, S07, and S02 are healthy; the rest are diabetic.

FIG. 11 is a plot showing the cumulative DPP-IV activity profile of pI discriminated isoforms from healthy and diabetic patients. Each point in the plot represents the cumulative percent of total activity as a function of the increasing pH of the continuous range of discriminated isoforms. As previously explained, DPP isoforms are discriminated by separating into discrete discriminated portions each associated with a particular narrow band of pH.

Figure 12:
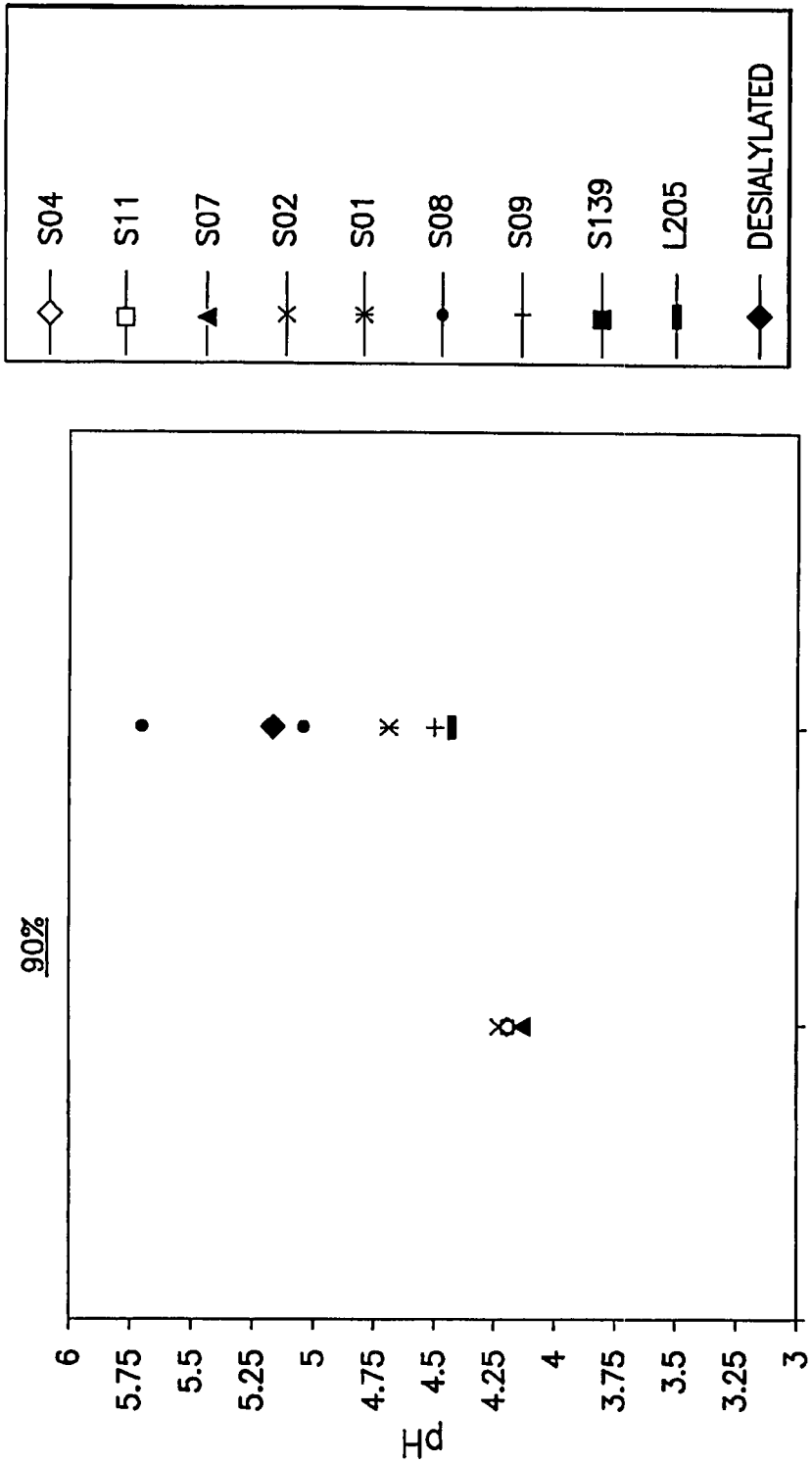
FIG. 12 is a plot of the pH at which the pI discriminated DPP-IV isoforms from each subject reaches a 90% DPP-IV activity. S04, S11, S07, and S02 are healthy; the rest are diabetic.

FIG. 12 shows the pH at which the cumulative activity from pI discriminated DPP-IV portions from individual patients reached 90% of the total activity for the measured range, summing up the activity of the discriminated isoform portions beginning from the acidic end of the measured pH range. The healthy patients reached 90% DPP-IV activity for isoforms discriminated at and below about pH 4.2. In contrast, the diabetic patients did not reach 90% DPP-IV activity for isoforms discriminated at and below about pH 4.4. The cumulative DPP-IV activity from sicker patients did not reach 90% of the total cumulative DPP-IV activity until taking into account isoforms discriminating at even higher pHs.

Thus, the pH at which the cumulative activity from pI discriminated DPP-IV portions from a sample reaches 90% total activity of the sample can be used to correlate DPP-IV activity measurement with disease. Thus, if the percent of total DPP-IV activity of all measured portions of the continuous range present in the isoforms discriminated at an isoelectric point associated with a pH range at and below about pH 4.4 does not exceed about 90%, then the presence of diabetes is detected. If at least about 10% of the total DPP-IV activity of all measured portions of the continuous range is present in the isoforms discriminated at an isoelectric point associated with a pH range at and above about pH 4.4, then the presence of diabetes is detected. The higher the pH above pH 4.4 at which 90% activity is reached is indicative of a more severe prognosis.

If at least about 90% of the total DPP-IV activity of all measured portions of the continuous range is present in the isoforms discriminated at an isoelectric point associated with a pH range at below about pH 4.2, then the absence of diabetes is detected. If the percent of total DPP-IV activity of all measured portions of the continuous range present in the isoforms discriminated at an isoelectric point associated with a pH range at and above about pH 4.2 does not exceed about 10%, then the absence of diabetes is detected.

Figure 13:
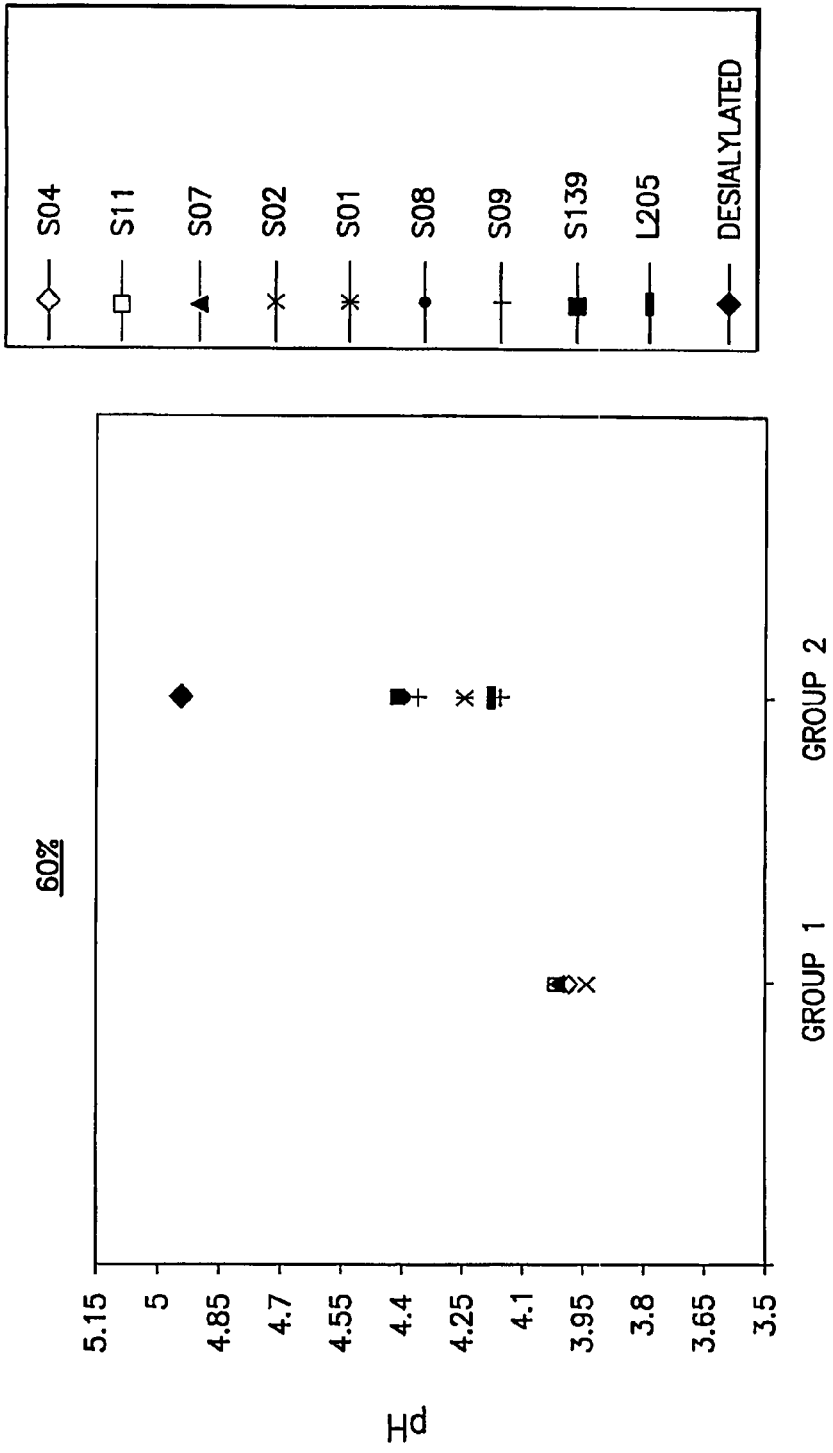
FIG. 13 is a plot of the pH at which the pI discriminated DPP-IV isoforms from each subject reaches a 60% DPP-IV activity. S04, S11, S07, and S02 are healthy; the rest are diabetic.

FIG. 13 shows the pH at which the cumulative activity from pI discriminated DPP-IV portions from individual patients reached 60% of the total activity, summing up the activity of isoforms beginning from the acidic end of the measured pH range. The healthy patients reached 60% DPP-IV activity at about pH 3.9. In contrast, the diabetic patients did not reach 60% DPP-IV activity until about pH 4.15 and above. The cumulative DPP-IV activity from sicker patients did not reach 60% of the total cumulative DPP-IV activity until taking into account isoforms discriminated at even higher pHs.

Thus, the pH at which the cumulative activity from pI discriminated DPP-IV portions from a sample reaches 60% total activity of the sample can be used to correlate DPP-IV activity measurement with disease. Thus, if the percent of total DPP-IV activity of all measured portions of the continuous range present in the isoforms discriminated at an isoelectric point associated with a pH range at and below about pH 4.15 does not exceed about 60%, then the presence of diabetes is detected. If at least about 40% of the total DPP-IV activity of all measured portions of the continuous range is present in the isoforms discriminated at an isoelectric point associated with a pH range at and above about pH 4.15, then the presence of diabetes is detected. The higher the pH above pH 4.15 at which 60% activity is reached is indicative of a more severe prognosis.

If at least about 60% of the total DPP-IV activity of all measured portions of the continuous range is present in the isoforms discriminated at an isoelectric point associated with a pH range at and below about pH 3.9, then the absence of diabetes is detected. If the percent of total DPP-IV activity of all measured portions of the continuous range present in the isoforms discriminated at an isoelectric point associated with a pH range at and above about pH 3.9 does not exceed about 40%, then the absence of diabetes is detected.

EXAMPLE 1

Using free form electrophoresis (FFE) (BD™ Free Flow Electrophoresis System), separating proteins based on charge, the isoforms of DPP-IV were separated into portions and characterized. The isolation of protein isoforms is preferred for examining the role of specific modifications on activity. Activity analysis indicates an increase in specific activity correlates with an increase in isoform pI. This suggests that posttranslational modifications may play a role in the regulation of DPP-IV activity. FFE may facilitate further studies that can correlate enzyme modification(s) to disease state.

FFE was performed using the BD™ Free Flow Electrophoresis System as follows: Porcine DPP-IV was obtained from Sigma™ (1-100 mg) were diluted (generally 1:5) in a pH-appropriate separation medium. The diluted proteins were then loaded at the most cathodic sample inlet of the Becton™ FFE chamber, and separated by application of 1200-1500V and 20-25 mA, with a separation medium flow rate of approximately 60 mL/h using a pH gradient of 3-10.

Figure 3:
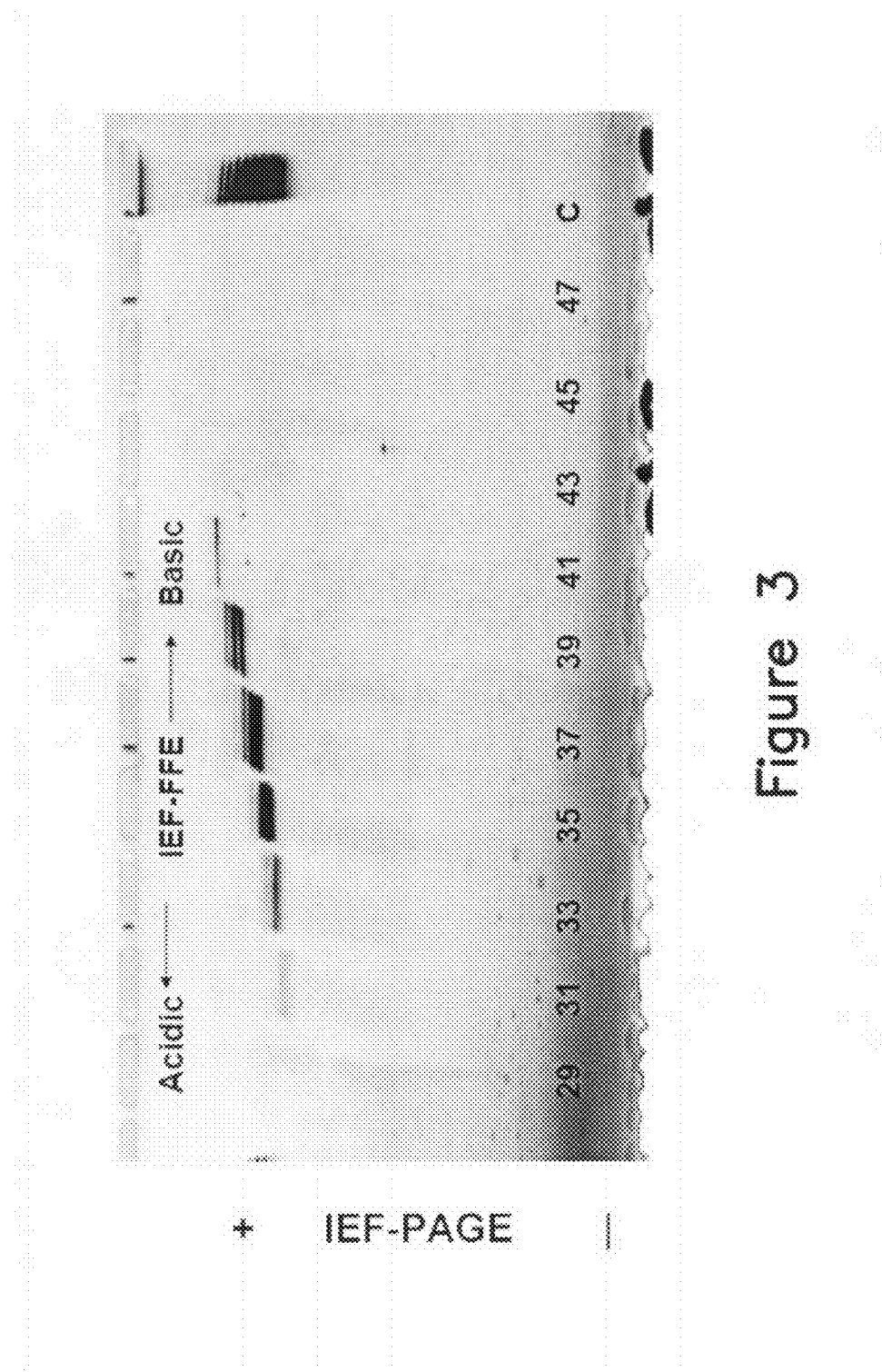
FIG. 3 is a silver-stained IEF acrylamide gel of fractions 27 to 47 from a native FFE (pH 3-10) separation of porcine DPP-IV.

Isoelectric Focusing (IEF)-FFE buffers and media were prepared according to manufacturers protocol (Becton™ FFE Application Manual) using native conditions with a pH gradient of 3-10. Isoelectric focusing poly acrylamide gel electrophoresis (PAGE) (IEF) was performed with custom-made gels with T:4%, or using blank Precoats™ (Serva) equilibrated at the appropriate pH range. Silver staining was performed to detect protein bands and the result is shown in FIG. 3.

Figure 2B:
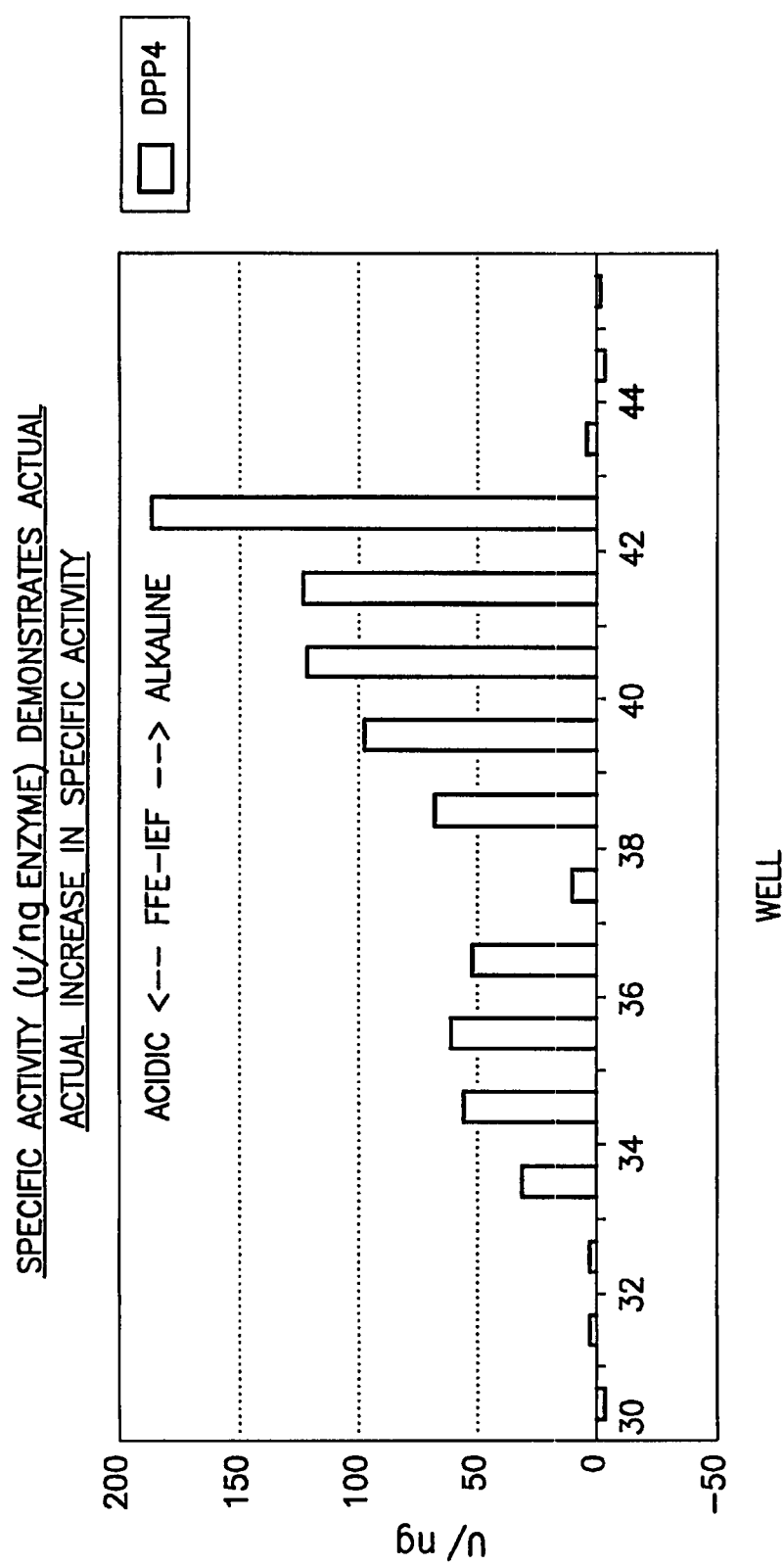
FIG. 2B shows the specific activity (U/ng enzyme) of discriminated porcine DPP-IV isoforms.

Activity assays were performed as follows: 45 µl of assay buffer (100 mM Tris-Cl [pH 8.0]; 0.05% v/v DMSO) was added to a 5 µl protein sample, and the increase in fluorescence was measured from Tinitial. Activity was expressed as the increase in Relative Fluorescence Units (RFU)/min resulting from hydrolysis of substrate Gly-Pro-AMC (250 µM) at 30° C. Results are shown in FIGS. 2A and 2B.

Trypsin digestion of proteins was performed by excision of Sypro Ruby stained bands that were visualized following PAGE(IEF) or SDS-PAGE and subsequent digestion according to kit recommendations (Pierce/Sigma).

Matrix-Assisted Laser Desorption/Ionization (MALDI) MS was performed as follows: Peptides were digested "in-gel" were extracted (as directed) and cleaned using ZipTip® Pipette Tips (Millipore). The digested peptides were mixed 1:1 with matrix (saturated solution of α-cyano-4-hydroxycinnamic acid in 60% acetonitrile) and spotted on a stainless steel target (Bruker Daltonics).

Figures 1, 4A:
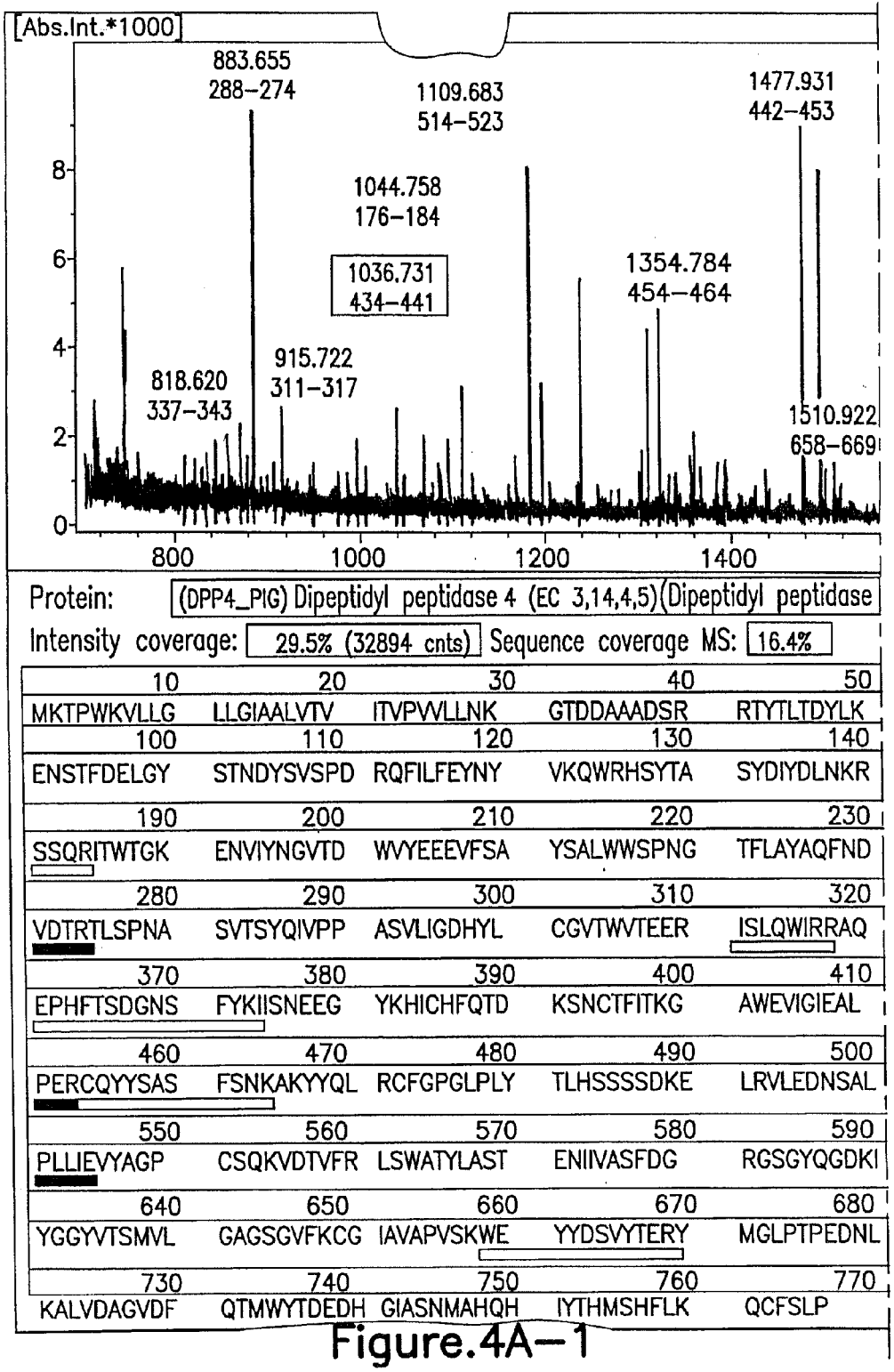
FIG. 1 depicts the workflow of a free-flow electrophoresis separation of isoforms.
FIGS. 4A and B (which includes the sequence designated as SEQ ID NO: 1) show the peptide mass fingerprint analysis of trypsinized protein bands excised from IEF gel for the most acidic (4A) and slightly more basic (4B) isoforms. Analysis of PMF identifies all isoforms as DPP-IV.
Figures 1, 4B:
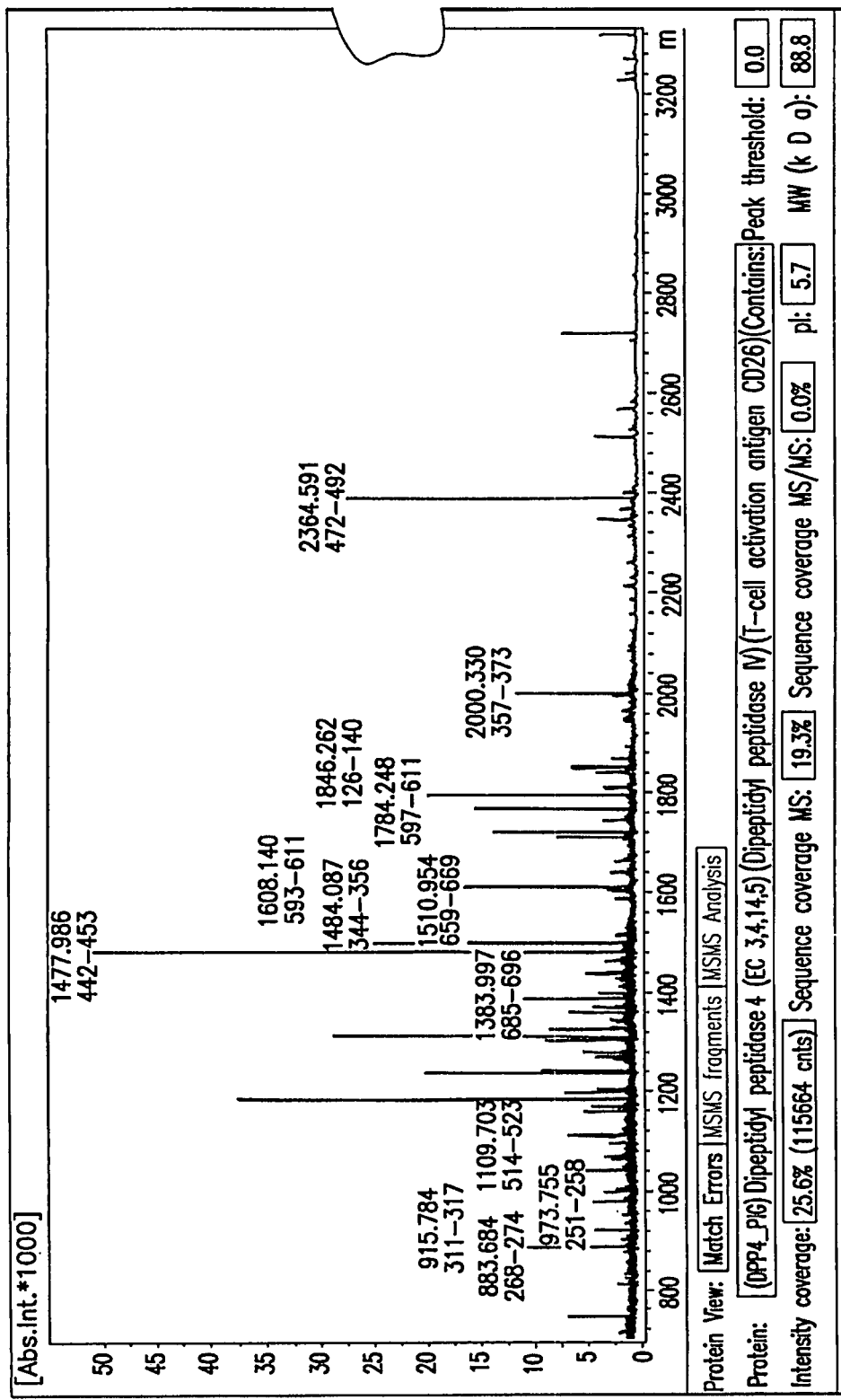
Figures 1, 5A:
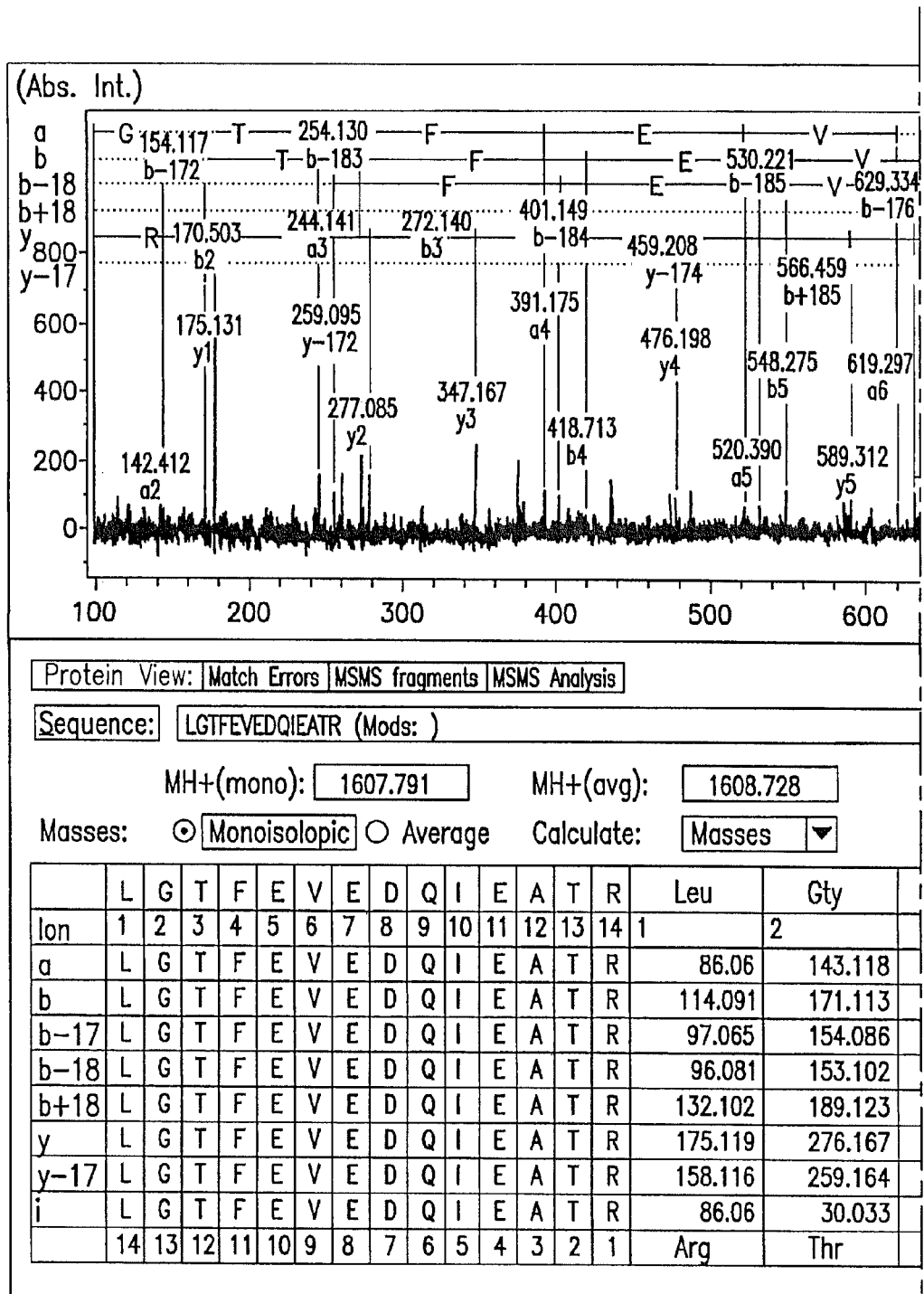
FIGS. 5A (which includes the sequence designated as SEQ ID NO: 2) and B (which includes the sequence designated as SEQ ID NO: 3) shows the confirmation of selected DPP-IV peaks with MALDI TOF/TOF.
Figures 2, 5A:
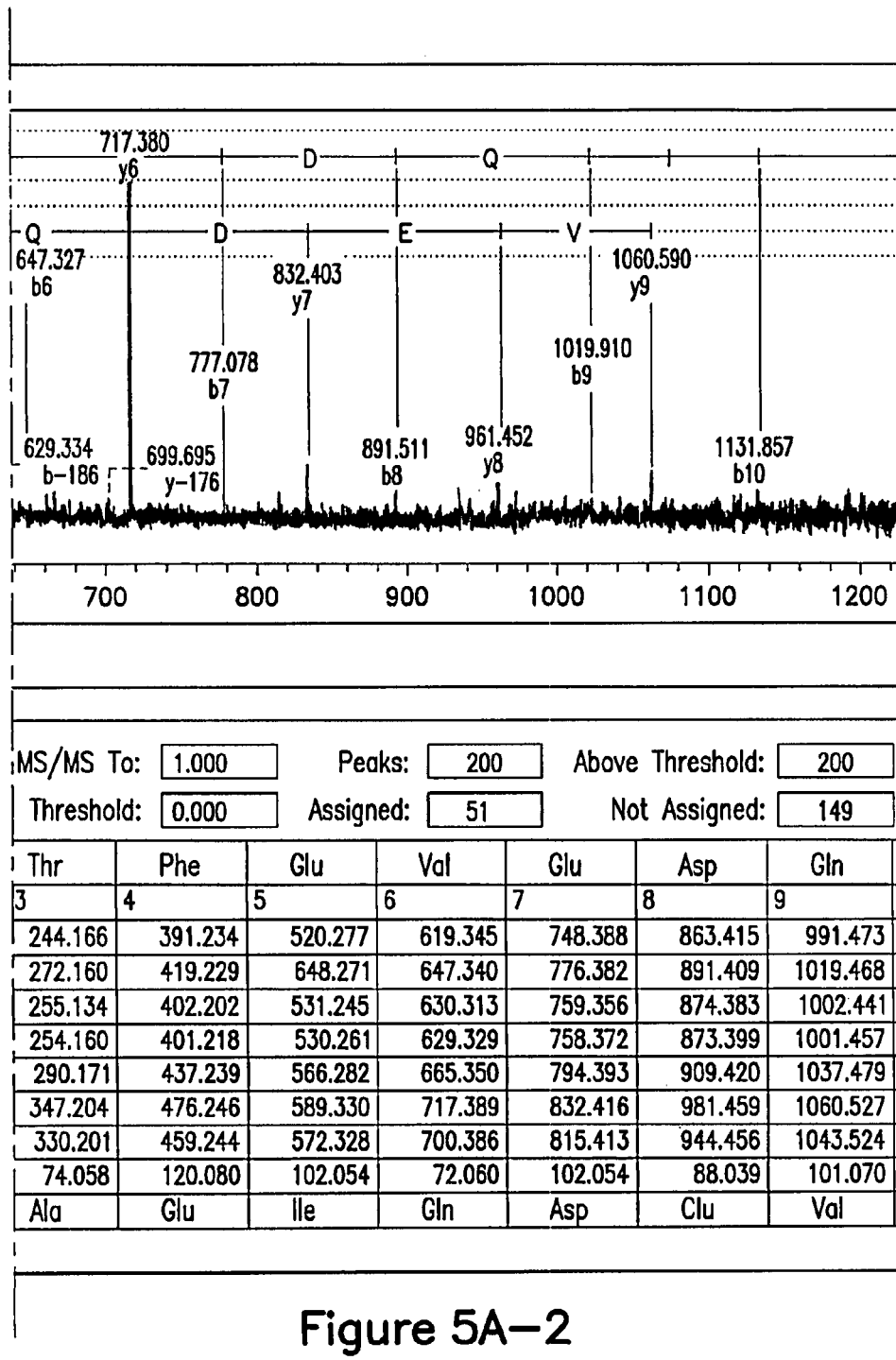
Figures 3, 5A:
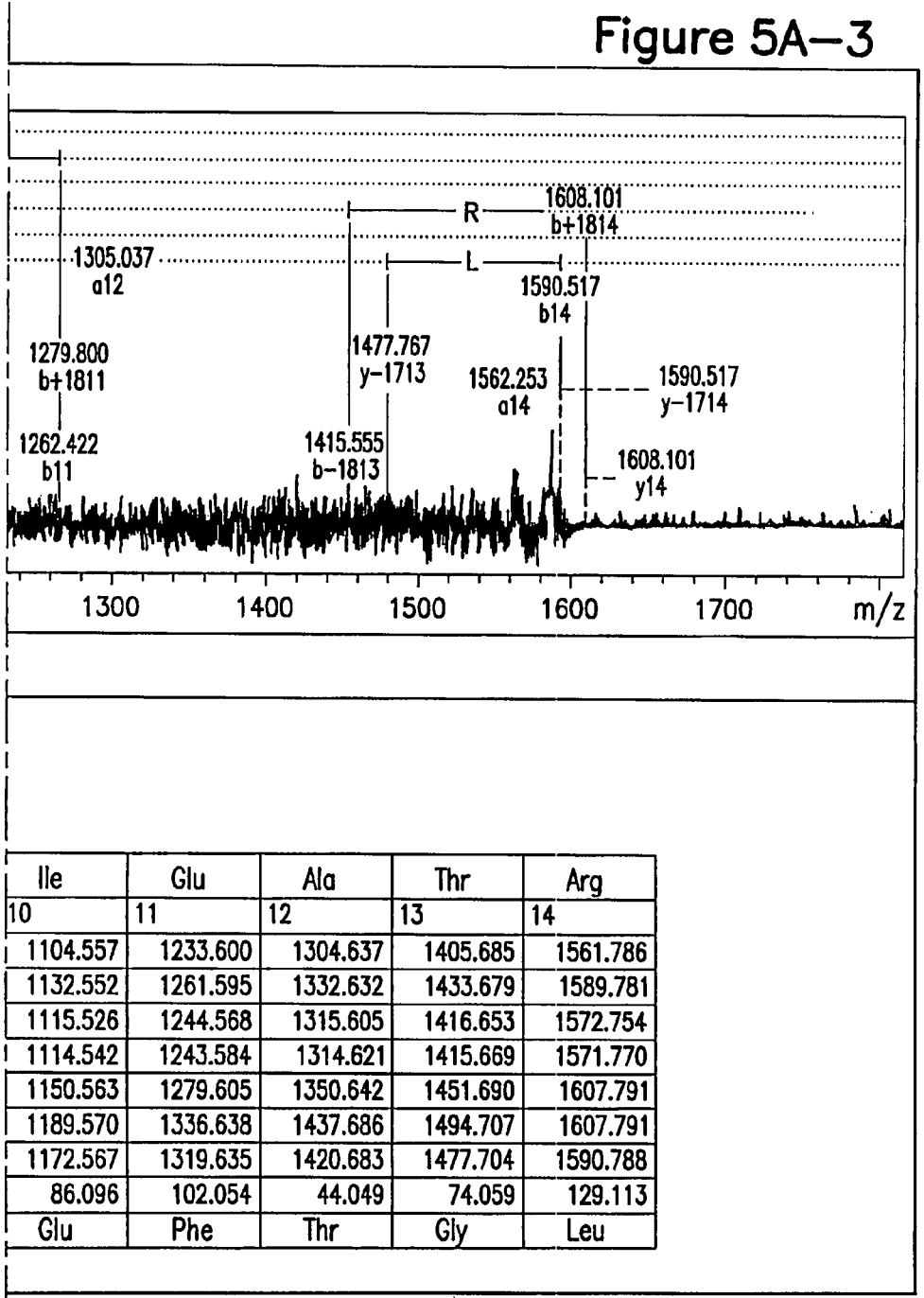
Figures 2, 5B:
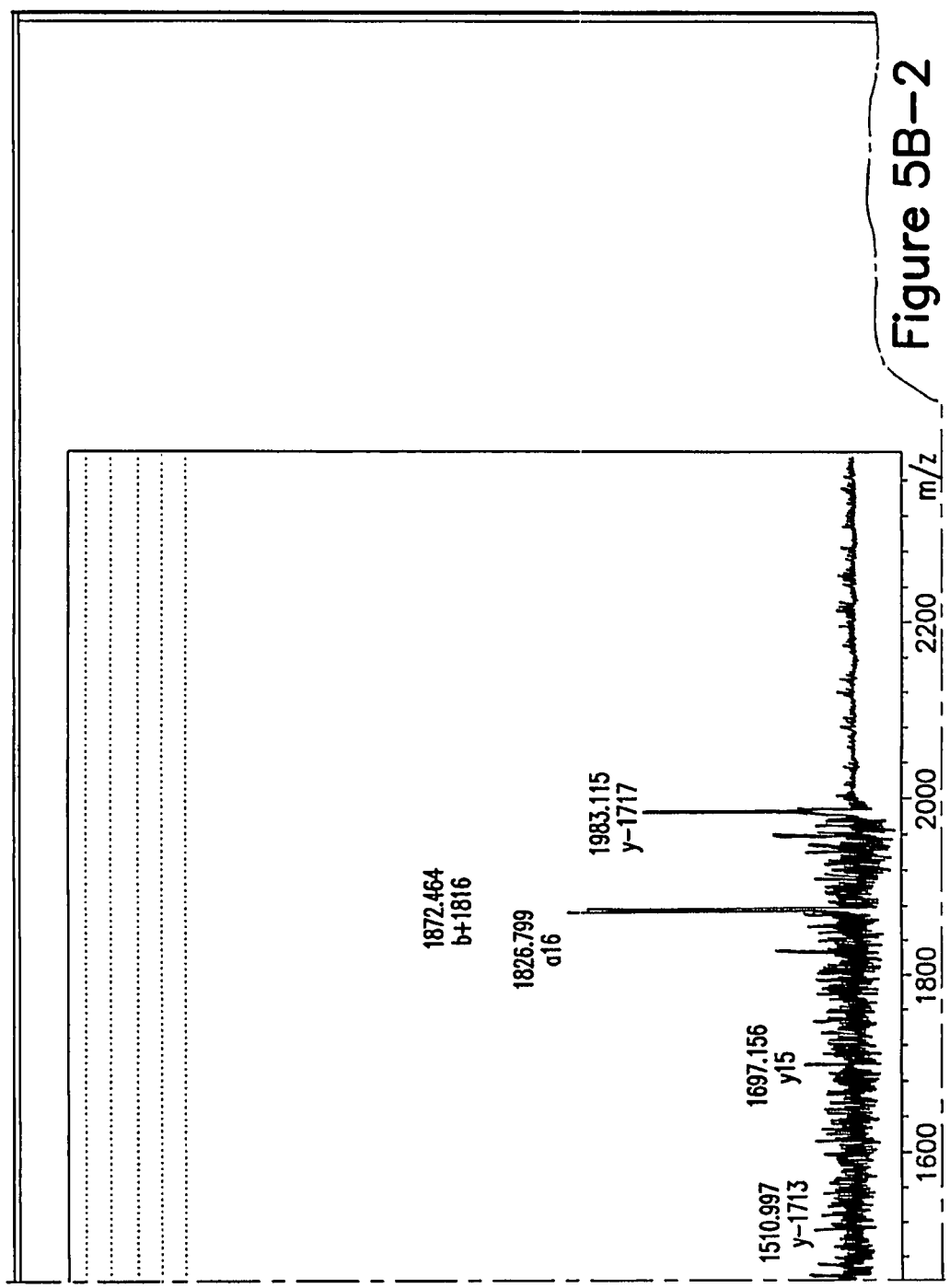
Figures 3, 5B:
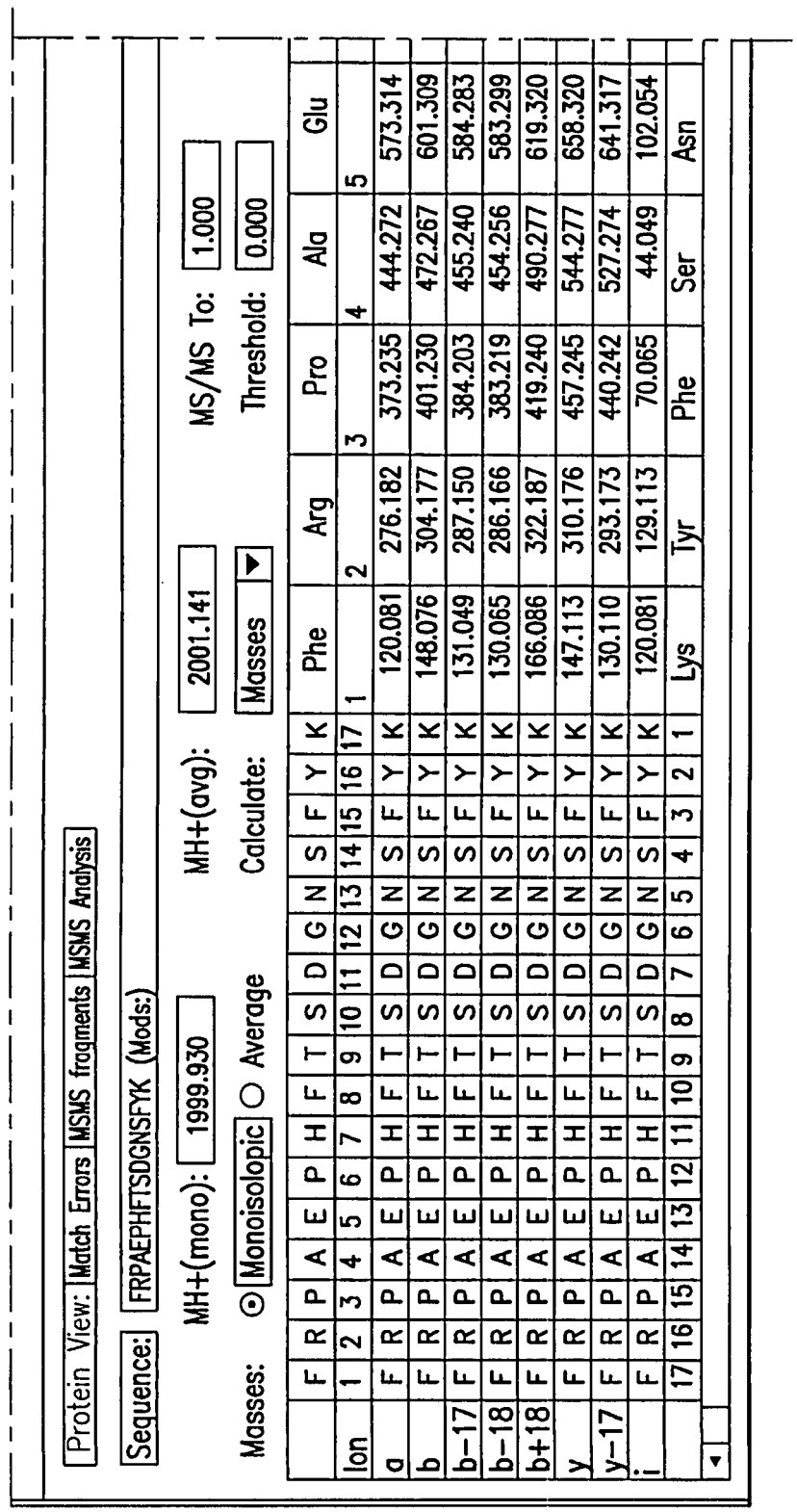

The initial MALDI-Time of Flight (TOF) Peptide Mass Fingerprints (PMF) were used to identify the digested proteins followed by TOF/TOF identification of specific peptides (both using Mascot). Results are shown in FIGS. 4A and 4B.

EXAMPLE 2

The experiments described in Example 2 followed the same protocol as presented in Example 1, except that the protein sample was derived from human plasma from healthy patients.

Human plasma samples (EDTA anti-coagulant) were obtained from two individuals, and DPP-IV isoforms were separated into portions as described in Example 1. Activity was measured as described in Example 1. The patterns of DPP-IV activity were examined to see if an activity profile, similar to porcine DPP-IV isoforms, exists. The results are presented in FIGS. 6A and 6B.

Figure 6A:
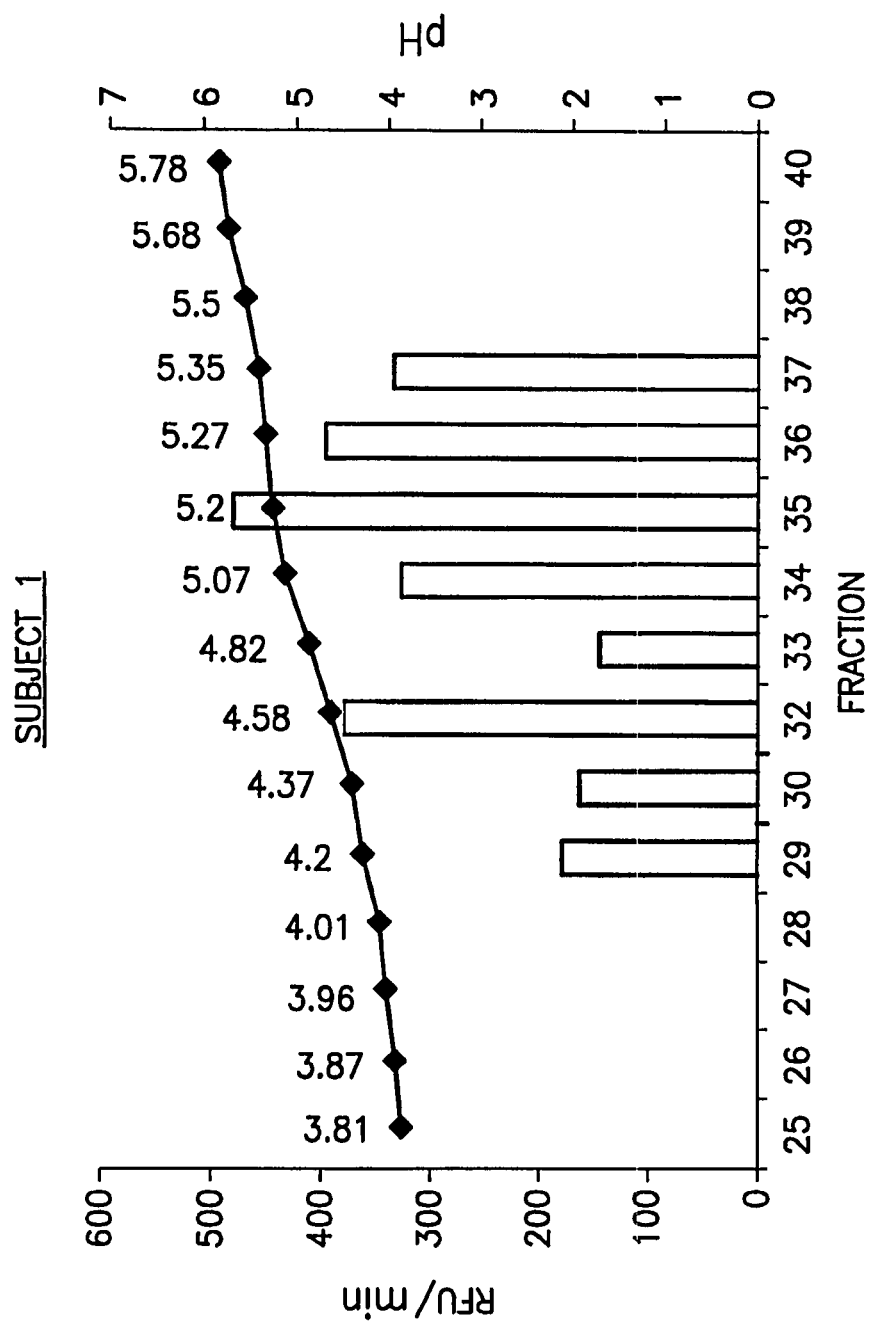
FIGS. 6A and B show the DPP-IV activity of FFE discriminated DPP-IV isoforms from human plasma in two healthy subjects.
Figure 6B:
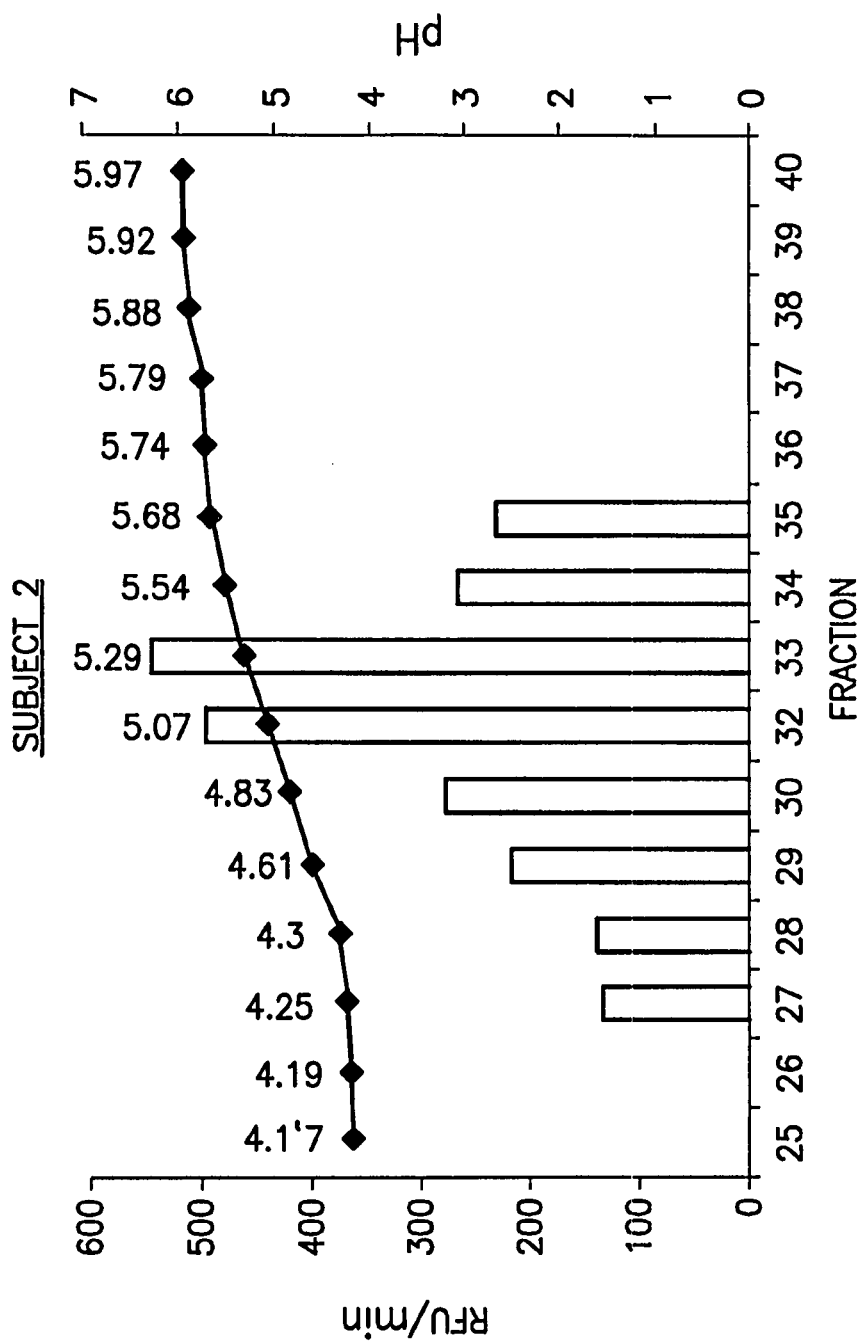

From the results reported in FIGS. 6A and 6B, it was observed that an activity spread similar to that seen with porcine DPP-IV for DPP-IV activity in human plasma. Increasing activity was observed at higher pH values (maximal approximately pH 5.2). Accurate protein (DPP-IV) quantification would be needed for determination of specific activity.

Through Examples 1 and 2, it is demonstrated that protein isoforms can be separated using FFE (IEF) and biochemical characterization of separate isoforms is enabled. The porcine DPP-IV model exhibits multiple isoforms (identified using Mass Spec) that exhibit different specific activities. Human DPP-IV (separated in plasma) exhibits a similar trend when analyzed following FFE. Posttranslational modifications (PTMs) may play a role in regulating DPP-IV specific activity. FFE may facilitate the identification and implications of potential PTMs for individual isoforms of DPP-IV as well as other proteins.

DPP-IV was measured as previously described. The results, presented in FIGS. 6A and 6B, when compared to the results from the DPP-IV porcine experiments indicate that human DPP-IV exhibits a similar activity trend when analyzed following FFE as the similarly analyzed porcine DPP-IV.

Taken in total, the results from examples 1 and 2 suggest that post-translational modifications (PTMs) may play a role in regulating DPP-IV specific activity and that FFE may facilitate the identification and implications of potential PTMs for individual isoforms of DPP-IV as well as other proteins.

EXAMPLE 3

The experiments described in Example 3 followed the same protocol as presented in Example 1, except that the protein sample was derived from human plasma, and IEF was performed with a pH gradient of 3-7. Specifically, 2 heparinized treated human plasma samples were obtained, one from a person with type-2 diabetes (glucose level of 538 mg/dL) and one from a healthy person.

Figure 7:
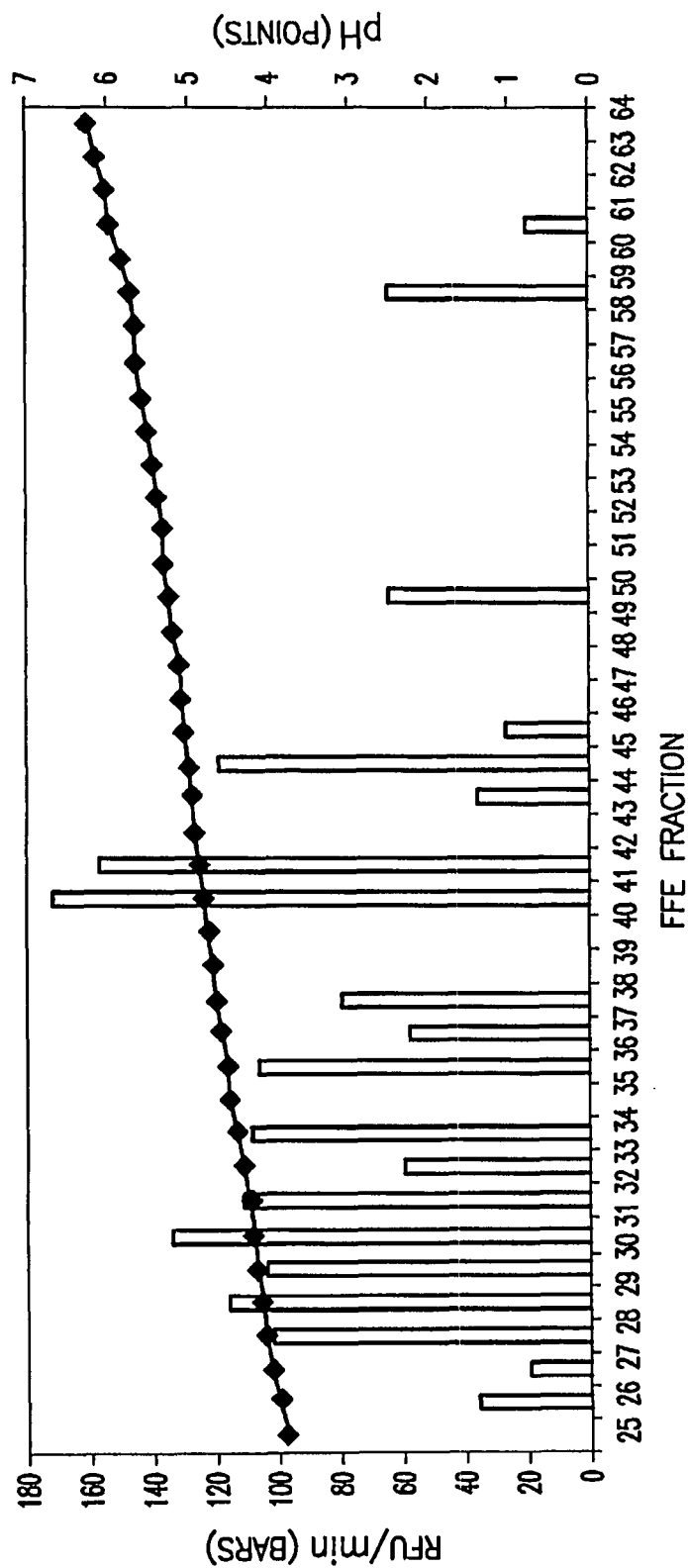
FIG. 7 shows the DPP-IV activity profile of FFE discriminated isoforms from a normal human subject.
Figure 8:
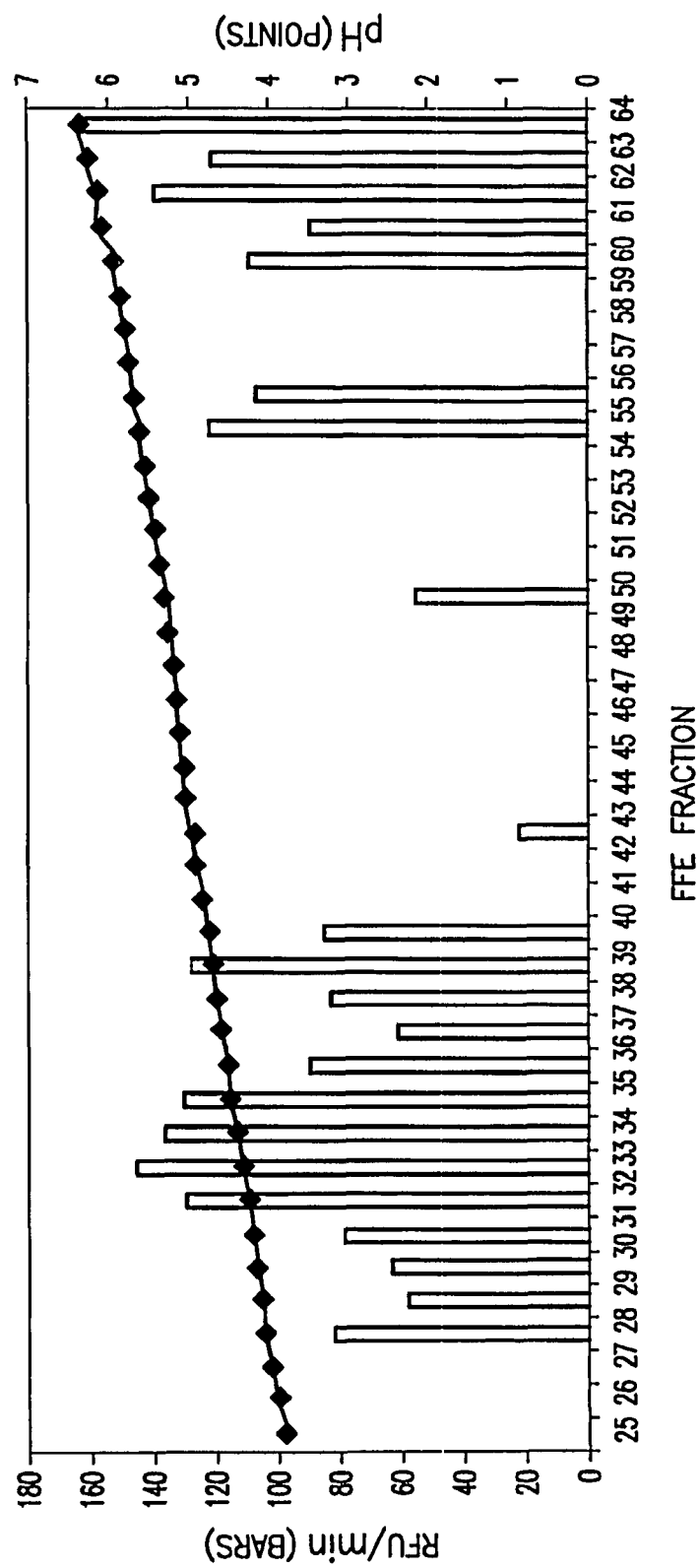
FIG. 8 shows the DPP-IV activity profile of FFE discriminated isoforms from a diabetic human subject with a glucose level of 538 mg/dL.

The results, presented in FIGS. 7 and 8, indicate that a DPP-IV isoform profile with a higher isoelectric range is exhibited by the diabetic sample.

EXAMPLE 4

The plasma from four healthy and five diabetic patients were discriminated by pI. FFE was performed using the Becton™ FFE chamber as follows: 25 µL plasma (diluted 1:8) was mixed with 25 µL glycerol, 25 µL 0.08% HPMC, 125 µL Separation Buffer pH 3-7. The diluted proteins were then loaded at the most cathodic sample inlet of the Becton™ FFE chamber, and separated by Interval Isoelectric Focusing (IIEF)-FFE using native conditions and a 3-7 pH range with application of 1200-1500V and 20-25 mA. IIEF-FFE was performed at 10° C. with a residence time totaling 64 minutes. A buffer flow rate of 50 mL/hr in 5 minute intervals (5 minutes forward then 5 minutes backward) totaling 60 minutes was used. Sample application was done at 6000 µL/hr for 2 min. with a media flow rate of 180 mL/hr during sample application. Following sample application the voltage was applied and the media flow rate was set to flow at 50 mL/hr in 5 minute intervals (5 min forward then 5 min backward) totaling 60 min. The sample was collected following Interval Separation by increasing the buffer flow forward to 300 mL/hr for 2 minutes, pausing, and then collecting for 2 minutes into 96 wells. DPP-IV activity was tested as outlined in Example 1. The results are shown in FIGS. 10 and 11.

In FIG. 10, the light bars represent the value obtained at each pI from one healthy patient, and the dark bars represent the average value obtained at each pI from one diabetic patient.

Two main peaks are observed in the healthy patients, at approximately pH 3.9 and approximately pH 4.1. Likewise, two main peaks are observed in the diabetic patients, at approximately pH 4.4 and approximately pH 4.8. The diabetic plasma profile is shifted to the higher pH, or to the right of the plasma profile from healthy patients.

In this example, Group 1 are healthy (S04, S11, S07, and S02) and Group 2 are diagnosed diabetics: L205—Blood Glucose=~139 mg/dL; S09—unknown Blood Glucose; S08—Blood Glucose=~90 mg/dL, patient's disease is managed on medication; S01—BG=~150 mg/dL; and S139—BG=~350 mg/dL.

Figure 9:
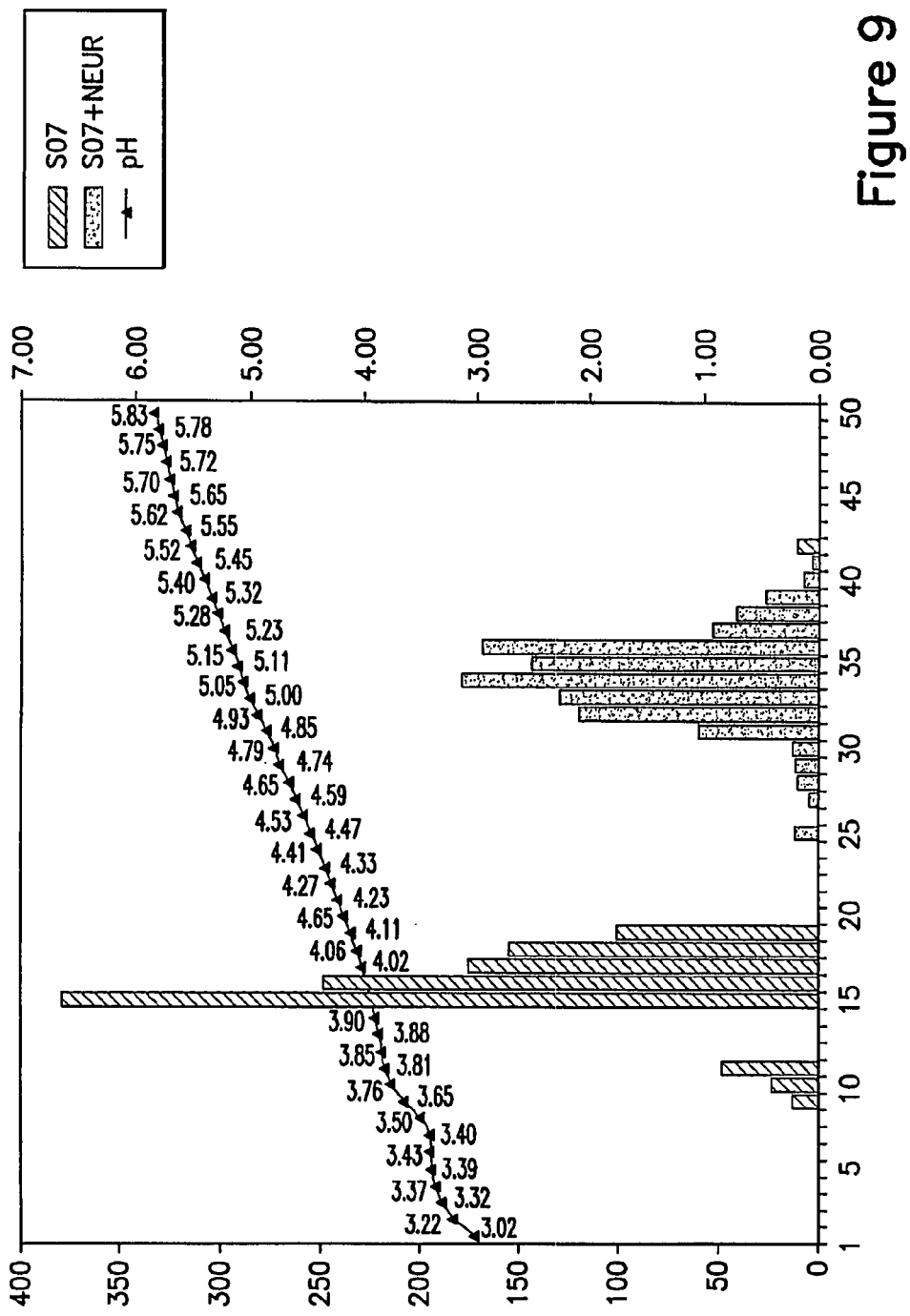
FIG. 9 shows an example of the DPP-IV profile shift resulting from desialylation of FFE discriminated isoforms from a healthy human patient. Activity is represented in RFU/min. The dark bars represent the treated sample; the lined bars represent the untreated sample.

An aliquot of plasma from a healthy subject was divided and one half was desialylated with neuraminidase and one left as a control. Each portion was separated under the conditions described above in this Example, and the isoform profile measured by enzyme analysis. The removal of sialic acid resulted in a shift of the profile from approximately pH 4.0 to approximately pH 5.0. The results are represented in a bar graph in FIG. 9.

Desialylation also resulted in a two to three fold increase in specific activity, as shown in Table 1.

TABLE 1

| | Specific DPP-IV activity (mU/mg) of | |
|---|---|---|
| Sample ID | Specific Activity Normal | Specific Activity Desialylated |
| S07 | 38.71 | 85.01 |
| S08 | 22.93 | 61.80 |
| S11 | 47.23 | 88.08 |

It appears that excess sialylation reduces the effectiveness (aka specific activity) of DPP-IV. Thus, one of the reasons why patients with different disease states may display different isoform profiles is due to post-translational modification, such as sialylation.

To account for actual pH gradients of the multiple samples, pH reading vs. % local activity (at that pH) was semi-integrated. Then, the percent activity along the pH range was added. This is shown in FIG. 11. Essentially, this allows the visualization of at what pH a certain "threshold" of activity was reached.

The healthy and diabetic data are shown at 60% in FIG. 12 and 90% at FIG. 13. The healthy patients all fall very tightly at pH 4.2 for 90% activity; while the diabetic patients all fall loosely above pH 4.4, and at higher pH with increasing severity of disease. The healthy patients all fall tightly at approximately pH 3.9 for 60% activity; while the diabetic patients all fall loosely above pH 4.15.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for diagnosis or prognosis of a metabolic disease state or condition, comprising:
   measuring at least one parameter of one or more discriminated portions of DPP-IV isoforms from a patient sample; and
   correlating said measured DPP-IV parameter with the presence, absence or severity of said metabolic disease state or condition,
   wherein said parameter comprises a member selected from the group consisting of DPP-IV activity, amount, concentration, post-translational modification type and post-translational modification amount.

2. The method of claim 1, wherein each portion contains one or more DPP-IV isoforms.

3. The method of claim 2, wherein each portion contains one DPP-IV isoform.

4. The method of claim 1, wherein one or more portions contain no DPP-IV isoforms, and other portions contain one or more DPP-IV isoforms.

5. The method of claim 1, wherein said parameter is DPP-IV activity, and said measuring is conducted via an assay which detects presence or amount of a hydrolysis product of the DPP-IV activity on a directly or indirectly detectable substrate.

6. The method of claim 5, wherein said substrate is X-Y-R, wherein X is any amino acid, Y is proline, alanine or arginine, and R is any detectable label.

7. The method of claim 1, wherein more than one DPP parameter is measured.

8. The method of claim 1, wherein said patient sample is selected from the group consisting of tissue, blood, plasma, serum, saliva, tears, mucus, urine, amniotic fluid, synovial joint fluid, seminal fluid, cerebrospinal fluid and combinations thereof.

9. The method of claim 1, further comprising communicating the presence, absence or severity of the disease state to an operator.

10. The method of claim 9, wherein said communicating comprises displaying the disease state in a medium selected from the group consisting of an electronic screen, a digital screen, a printable substrate, and an audible signal.

11. The method of claim 1, further comprising discriminating DPP-IV portions of DPP-IV present in the patient sample.

12. The method of claim 11, wherein said discriminating is performed prior to said measuring.

13. The method of claim 11, wherein said discriminating is performed simultaneously with said measuring.

14. The method of claim 1, wherein said patient sample is processed prior to said measuring.

15. The method of claim 14, wherein said processing is selected from the group consisting of homogenizing, diluting, concentrating, freezing and combinations thereof.

16. The method of claim 11, wherein said discriminating is performed by physical separation or isolation.

17. The method of claim 16, wherein said discriminating is performed using a gel-free format.

18. The method of claim 17, wherein said gel-free format is selected from the group consisting of free-flow electrophoresis and matrix-free electrophoresis.

19. The method of claim 11, wherein said DPP-IV portions are discriminated based on the isoelectric point of DPP-IV isoforms.

20. The method of claim 11, wherein there are at least two said DPP-IV portions.

21. The method of claim 1, wherein said correlating comprises comparing the measured parameter to the corresponding parameter of a standard.

22. The method of claim 1, wherein said correlating comprises comparing the measured parameter to the corresponding parameter of an internal control.

23. The method of claim 20, wherein said parameter is measured for said at least two portions.

24. The method of claim 23, wherein said correlating comprises comparing the parameter of at least one portion to the total measured corresponding parameter for at least two portions.

25. The method of claim 24, wherein said correlating comprises comparing the parameter of at least one portion to the total measured corresponding parameter for all portions.

26. The method of claim 23, wherein said correlating comprises comparing the measured parameter of at least one portion to the corresponding measured parameter of at least one other portion.

27. The method of claim 23, wherein said correlating comprises comparing the total measured parameter for two or more portions to the corresponding total parameter of a standard.

28. The method of claim 23, wherein said correlating comprises comparing the total measured parameter for two or more portions to the corresponding total parameter of an internal control.

29. A method for diagnosis or prognosis of a type II diabetes, comprising:
measuring at least one parameter of one or more discriminated portions of DPP-IV isoforms from a patient sample, wherein said DPP-IV parameter is selected from the group consisting of DPP-IV activity, amount, concentration, post-translational modification type and post-translational modification amount; and
correlating said measured parameter with the presence, absence or severity of type II diabetes.

30. The method of claim 29, wherein each measured portion contains one or more DPP-IV isoforms.

31. The method of claim 29, wherein each measured portions contains one DPP-IV isoform.

32. The method of claim 29, wherein one or more portions contain no DPP-IV isoforms, and other portions contain one or more DPP-IV isoforms.

33. The method of claim 29, wherein more than one DPP-IV parameter is measured.

34. The method of claim 29, wherein said DPP-IV activity is measured via an assay which detects presence or amount of a hydrolysis product of the DPP-IV activity on a labeled substrate.

35. The method of claim 34, wherein said substrate is X-Y-R, wherein X is any amino acid, Y is alanine, praline or arginine, and R is any detectable label.

36. The method of claim 33, wherein said more than one DPP-IV parameter is selected from the group consisting of amount, concentration, activity, expression, post-translational modification type and post-translational modification amount.

37. The method of claim 29, wherein said patient sample is selected from the group consisting of blood, plasma, serum and combinations thereof.

38. The method of claim 29, further comprising communicating the presence, absence or severity of type II diabetes to an operator.

39. The method of claim 29, further comprising discriminating DPP-IV into portions.

40. The method of claim 39, wherein said discriminating is performed prior to said measuring.

41. The method of claim 29, wherein said DPP-IV isoforms are discriminated on the basis of isoelectric point.

42. The method of claim 29, wherein the DPP-IV activity of a continuous range of portions is measured.

43. The method of claim 42, further comprising obtaining an activity profile over the continuous range of portions.

44. The method of claim 43, wherein the presence of type II diabetes is correlated with an activity profile feature selected from the group consisting of:
a. the percent of total DPP-IV activity of all measured portions of the continuous range present in the isoforms discriminated at an isoelectric point associated with a pH range at and below about pH 4.4 does not exceed about 90%;
b. the percent of the total DPP-IV activity of all measured portions of the continuous range present in the isoforms discriminated at an isoelectric point associated with a pH range at and below about pH 4.15 does not exceed about 60%;
c. at least about 10% of the total DPP-IV activity of all measured portions of the continuous range is present in the isoforms discriminated at an isoelectric point associated with a pH range at and above about pH 4.4;
d. at least about 40% of the total DPP-IV activity of all measured portions of the continuous range is present in the isoforms discriminated at an isoelectric point associated with a pH range at and above about pH 4.15;
e. a peak of the DPP-IV activity profile at about pH 4.4, wherein said peak is associated with at least about 10% of the total measured activity of the continuous range;
f. a peak of DPP-IV activity profile at about pH 4.8, wherein said peak is associated with at least about 10% of the total measured activity of the continuous range;
g. a shift in DPP-IV activity profile to higher pH compared to an internal negative control;
h. a shift in DPP-IV activity profile to higher pH compared to a negative standard; and
i. combinations thereof.

45. The method of claim 43, wherein the absence of type II diabetes is correlated with an activity profile feature selected from the group consisting of:
a. at least about 90% of the total DPP-IV activity of all measured portions of the continuous range is present in the isoforms discriminated at an isoelectric point associated with a pH range at and below about pH 4.2;
b. at least about 60% of the total DPP-IV activity of all measured portions of the continuous range is present in the isoforms discriminated at an isoelectric point associated with a pH range at and below about pH 3.9;
c. the percent of total DPP-IV activity of all measured portions of the continuous range present in the isoforms discriminated at an isoelectric point associated with a pH range at and above about pH 4.2 does not exceed about 10%;
d. the percent of the total DPP-IV activity of all measured portions of the continuous range present in the isoforms discriminated at an isoelectric point associated with a pH range at and above about pH 3.9 does not exceed about 40%;
e. a shift in DPP-IV activity profile to lower pH compared to an internal positive control;
f. a shift in DPP-IV activity profile to lower pH compared to a positive standard; and
g. combinations thereof.

46. The method of claim 1 or claim 29, wherein said parameter is post-translational modification type.

47. The method of claim 1 or claim 29, wherein said parameter is post-translational modification amount.

* * * * *

SEQUENCE LISTING

<160> NUMBER OF SEQ ID NOS: 3

<210> SEQ ID NO 1
<211> LENGTH: 766
<212> TYPE: PRT
<213> ORGANISM: Unknown

-continued

```
<220> FEATURE:
<223> OTHER INFORMATION: Dipeptidyl peptidase IV; IUBMB Enzyme
      Nomenclature EC 3.14.4.5

<400> SEQUENCE: 1

Met Lys Thr Pro Trp Lys Val Leu Leu Gly Leu Leu Gly Ile Ala Ala
1               5                   10                  15

Leu Val Thr Val Ile Thr Val Pro Val Val Leu Leu Asn Lys Gly Thr
            20                  25                  30

Asp Asp Ala Ala Ala Asp Ser Arg Arg Thr Tyr Thr Leu Thr Asp Tyr
        35                  40                  45

Leu Lys Ser Thr Phe Arg Val Lys Phe Tyr Thr Leu Gln Trp Ile Ser
50                  55                  60

Asp His Glu Tyr Leu Tyr Lys Gln Glu Asn Asn Ile Leu Leu Phe Asn
65                  70                  75                  80

Ala Glu Tyr Gly Asn Ser Ser Ile Phe Leu Glu Asn Ser Thr Phe Asp
                85                  90                  95

Glu Leu Gly Tyr Ser Thr Asn Asp Tyr Ser Val Ser Pro Asp Arg Gln
            100                 105                 110

Phe Ile Leu Phe Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Ile Thr Trp Ser Pro Val
145                 150                 155                 160

Gly His Lys Leu Ala Tyr Val Trp Asn Asn Asp Ile Tyr Val Lys Asn
                165                 170                 175

Glu Pro Asn Leu Ser Ser Gln Arg Ile Thr Trp Thr Gly Lys Glu Asn
            180                 185                 190

Val Ile Tyr Asn Gly Val Thr Asp Trp Val Tyr Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Ile Pro Tyr
                245                 250                 255

Pro Lys Ala Gly Ala Glu Asn Pro Thr Val Lys Phe Phe Val Val Asp
            260                 265                 270

Thr Arg Thr Leu Ser Pro Asn Ala Ser Val Thr Ser Tyr Gln Ile Val
        275                 280                 285

Pro Pro Ala Ser Val Leu Ile Gly Asp His Tyr Leu Cys Gly Val Thr
    290                 295                 300

Trp Val Thr Glu Glu Arg Ile Ser Leu Gln Trp Ile Arg Arg Ala Gln
305                 310                 315                 320

Asn Tyr Ser Ile Ile Asp Ile Cys Asp Tyr Asp Glu Ser Thr Gly Arg
                325                 330                 335

Trp Ile Ser Ser Val Ala Arg Gln His Ile Glu Ile Ser Thr Thr Gly
            340                 345                 350

Trp Val Gly Arg Phe Arg Pro Ala Glu Pro His Phe Thr Ser Asp Gly
        355                 360                 365

Asn Ser Phe Tyr Lys Ile Ile Ser Asn Glu Glu Gly Tyr Lys His Ile
    370                 375                 380

Cys His Phe Gln Thr Asp Lys Ser Asn Cys Thr Phe Ile Thr Lys Gly
385                 390                 395                 400
```

```
Ala Trp Glu Val Ile Gly Ile Glu Ala Leu Thr Ser Asp Tyr Leu Tyr
                405                 410                 415

Tyr Ile Ser Asn Glu His Lys Gly Met Pro Gly Gly Arg Asn Leu Tyr
            420                 425                 430

Arg Ile Gln Leu Asn Asp Tyr Thr Lys Val Thr Cys Leu Ser Cys Glu
                435                 440                 445

Leu Asn Pro Glu Arg Cys Gln Tyr Tyr Ser Ala Ser Phe Ser Asn Lys
        450                 455                 460

Ala Lys Tyr Tyr Gln Leu Arg Cys Phe Gly Pro Gly Leu Pro Leu Tyr
465                 470                 475                 480

Thr Leu His Ser Ser Ser Asp Lys Glu Leu Arg Val Leu Glu Asp
                    485                 490                 495

Asn Ser Ala Leu Asp Lys Met Leu Gln Asp Val Gln Met Pro Ser Lys
                500                 505                 510

Lys Leu Asp Val Ile Asn Leu His Gly Thr Lys Phe Trp Tyr Gln Met
            515                 520                 525

Ile Leu Pro Pro His Phe Asp Lys Ser Lys Lys Tyr Pro Leu Leu Ile
        530                 535                 540

Glu Val Tyr Ala Gly Pro Cys Ser Gln Lys Val Asp Thr Val Phe Arg
545                 550                 555                 560

Leu Ser Trp Ala Thr Tyr Leu Ala Ser Thr Glu Asn Ile Ile Val Ala
                    565                 570                 575

Ser Phe Asp Gly Arg Gly Ser Gly Tyr Gln Gly Asp Lys Ile Met His
                580                 585                 590

Ala Ile Asn Arg Arg Leu Gly Thr Phe Glu Val Glu Asp Gln Ile Glu
            595                 600                 605

Ala Thr Arg Gln Phe Ser Lys Met Gly Phe Val Asp Asp Lys Arg Ile
        610                 615                 620

Ala Ile Trp Gly Trp Ser Tyr Gly Gly Tyr Val Thr Ser Met Val Leu
625                 630                 635                 640

Gly Ala Gly Ser Gly Val Phe Lys Cys Gly Ile Ala Val Ala Pro Val
                    645                 650                 655

Ser Lys Trp Glu Tyr Tyr Asp Ser Val Tyr Thr Glu Arg Tyr Met Gly
                660                 665                 670

Leu Pro Thr Pro Glu Asp Asn Leu Asp Tyr Tyr Arg Asn Ser Thr Val
            675                 680                 685

Met Ser Arg Ala Glu Asn Phe Lys Gln Val Glu Tyr Leu Leu Ile His
        690                 695                 700

Gly Thr Ala Asp Asp Asn Val His Phe Gln Gln Ser Ala Gln Leu Ser
705                 710                 715                 720

Lys Ala Leu Val Asp Ala Gly Val Asp Phe Gln Thr Met Trp Tyr Thr
                    725                 730                 735

Asp Glu Asp His Gly Ile Ala Ser Asn Met Ala His Gln His Ile Tyr
                740                 745                 750

Thr His Met Ser His Phe Leu Lys Gln Cys Phe Ser Leu Pro
            755                 760                 765

<210> SEQ ID NO 2
<211> LENGTH: 14
<212> TYPE: PRT
<213> ORGANISM: Unknown
<220> FEATURE:
<223> OTHER INFORMATION: Fragmented ion of DPP 4 (Dipeptidyl peptidase
      4) generated by MALDI TOF/TOF that is also read in the reverse
      order.
```

```
<400> SEQUENCE: 2

Leu Gly Thr Phe Glu Val Glu Asp Gln Ile Glu Ala Thr Arg
1               5                   10

<210> SEQ ID NO 3
<211> LENGTH: 17
<212> TYPE: PRT
<213> ORGANISM: Unknown
<220> FEATURE:
<223> OTHER INFORMATION: Fragmented ion of DPP 4 (Dipeptidyl peptidase
      4) generated by MALDI TOF/TOF that is also read in the reverse
      order.

<400> SEQUENCE: 3

Phe Arg Pro Ala Glu Pro His Phe Thr Ser Asp Gly Asn Ser Phe Tyr
1               5                   10                  15

Lys
```